(12) United States Patent
Zhang et al.

(10) Patent No.: US 10,414,744 B2
(45) Date of Patent: Sep. 17, 2019

(54) 4-SULFUR PENTAFLUORIDE PHENOL COMPOUND AND PREPARATION METHOD THEREFOR, AND PREPARATION METHOD FOR SULFUR PENTAFLUORIDE SUBSTITUTED BENZOPYRAN COMPOUND

(71) Applicant: GUANGZHOU INSTITUTES OF BIOMEDICINE AND HEALTH CHINESE ACADEMY OF SCIENCES, Guangdong (CN)

(72) Inventors: Yanmei Zhang, Guangdong (CN); John J. Talley, Guangdong (CN); Yican Wang, Guangdong (CN); Chuang He, Guangdong (CN); Jiantong Guan, Guangdong (CN); Yongjie Lin, Guangdong (CN); Micky D. Tortorella, Guangdong (CN)

(73) Assignee: GUANGZHOU INSTITUTES OF BIOMEDICINE AND HEALTH CHINESE ACADEMY OF SCIENCES, Guangdong (CN)

( * ) Notice: Subject to any disclaimer, the term of this patent is extended or adjusted under 35 U.S.C. 154(b) by 0 days.

(21) Appl. No.: 16/083,485

(22) PCT Filed: Jun. 22, 2016

(86) PCT No.: PCT/CN2016/086772
§ 371 (c)(1),
(2) Date: Sep. 7, 2018

(87) PCT Pub. No.: WO2017/152539
PCT Pub. Date: Sep. 14, 2017

(65) Prior Publication Data
US 2019/0084957 A1    Mar. 21, 2019

(30) Foreign Application Priority Data

Mar. 9, 2016 (CN) .......................... 2016 1 0133812

(51) Int. Cl.
*C07D 311/70* (2006.01)
*C07D 311/58* (2006.01)
*C07D 405/06* (2006.01)
*C07C 319/00* (2006.01)
*C07C 323/20* (2006.01)
*C07C 319/20* (2006.01)

(52) U.S. Cl.
CPC .......... *C07D 311/70* (2013.01); *C07C 319/00* (2013.01); *C07C 319/20* (2013.01); *C07C 323/20* (2013.01); *C07D 311/58* (2013.01); *C07D 405/06* (2013.01)

(58) Field of Classification Search
CPC .................................................... C07D 311/70
USPC ......................................................... 549/408
See application file for complete search history.

(56) References Cited

U.S. PATENT DOCUMENTS

2015/0109011 A1    4/2015   Lindsey et al.

FOREIGN PATENT DOCUMENTS

| CN | 105585547 A | 5/2016 |
|---|---|---|
| WO | 2015109011 A1 | 7/2015 |

OTHER PUBLICATIONS

Morrison et al., Org. Chem. 3rd edition, 1973, pp. 349, 510-511, 636.*
International Search Report cited in PCT/CN2016/086772, dated Nov. 30, 2016, 2 pages.

* cited by examiner

*Primary Examiner* — Taofiq A Solola
(74) *Attorney, Agent, or Firm* — Workman Nydegger

(57) ABSTRACT

Provided are a 4-sulfur pentafluoride phenol compound and a preparation method therefor, and a preparation method for a sulfur pentafluoride substituted benzopyran compound. According to the present invention, sulfur pentafluoride salicylaldehyde with multiple substituent groups is synthesized through a plurality of steps by using sulfur pentafluoride phenol as a raw material, and then the sulfur pentafluoride substituted benzopyran compound is synthesized on this basis. The method is simple and convenient, and low in cost; overcomes the defects that, at present, the number of types of sulfur pentafluoride phenols is small, and the synthesis of various sulfur pentafluoride substituted benzopyran compounds cannot be met; and has wide industrial application prospects.

17 Claims, No Drawings

4-SULFUR PENTAFLUORIDE PHENOL COMPOUND AND PREPARATION METHOD THEREFOR, AND PREPARATION METHOD FOR SULFUR PENTAFLUORIDE SUBSTITUTED BENZOPYRAN COMPOUND

TECHNICAL FIELD

The present disclosure belongs to the field of medicine preparation, and relates to a 4-sulfur pentafluoride phenol-based compound and a preparation method thereof, and a preparation method for a sulfur pentafluoride substituted benzopyran-based compound.

BACKGROUND

Inflammation is a common and frequently-occurring disease that endangers human health and affects the quality of human life. The most common inflammation is arthritis, and there are currently approximately 355 million patients suffering from arthritis all over the world. It is estimated that there are approximately 100 million patients suffering from arthritis in China, and this number is increasing every year. Therefore, the development of anti-inflammatory and analgesic drugs is of great significance.

Traditional non-steroidal anti-inflammatory drugs, including ibuprofen and diclofenac, are the main drugs for the treatment of arthritis. However, while exerting analgesic and anti-inflammatory effects, such drugs also bring about a variety of serious adverse reactions and complications to the digestive tract, such as epigastric discomfort, ulceration, gastrointestinal hemorrhage, perforation and intestinal obstruction, and the like.

Cyclooxygenase (COX) is a major target for non-steroidal anti-inflammatory drugs. COX has two isomers, i.e., COX-1 and COX-2. Although the two isomers have 60% homology in structure, they have different distributions in tissue cells and different biological functions. COX-1 exists in normal tissues, catalyzes the synthesis of PGE2 and PGI2, and has functions of cell stabilization and cytoprotection, whereas COX-2 is cytokine-inducible and it only exists in damaged tissues. The prostaglandin catalytically synthesized by COX-2 is proinflammatory and has an inflammatory and pain-causing effect. It is believed by most scholars that traditional non-steroidal anti-inflammatory drugs inhibit both COX-1 and COX-2, and inhibition of COX-1 leads to a variety of serious adverse reactions and complications in digestive tract. Therefore, searching for inhibitors that selectively inhibit COX-2 has become the main direction of research and development.

Coxib non-steroidal anti-inflammatory drugs such as celecoxib, rofecoxib, and valdecoxib are representatives of this type of selective inhibitors for COX-2. They can selectively inhibit COX-2 without acting on COX-1, minimizing the intestinal side effects while exerting their anti-inflammatory effects. However, they also have deficiencies, for example, it has been identified that rofecoxib will cause cardiovascular risk, therefore it has been withdrawn globally. Celecoxib is also required to be used with caution due to the presence of cardiovascular risk in some patients.

Although the cardiovascular risk of coxib drugs has an impact on COX-2 inhibitory non-steroidal anti-inflammatory drugs, most studies have suggested that for COX-2 inhibitory drugs, since their chemical structures are different, their safeties are completely different. Some COX-2 inhibitory drugs even have a potential protective effect on angiocarpy. Currently, there are approximately hundreds of millions of people taking non-steroidal anti-inflammatory drugs worldwide, and COX-2 inhibitors are an important part among them. Although the COX-2 families have "bad guys" with serious adverse reactions, they have played a huge role in relieving the patient's conditions, and there is no better alternative drugs having been found yet currently. Therefore, the development of COX-2 inhibitors remains an important direction for anti-inflammatory and analgesic drugs.

A sulfur pentafluoride substituted benzopyran-based compound is derived from a bisaryl heterocyclic coxib compound, has the same pharmaceutical effect and selectivity as a bisaryl heterocyclic coxib compound, i.e., has a selective inhibition effect on the COX-2 enzyme, and its structural formula is as follows:

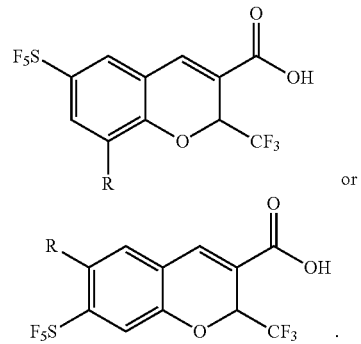

CN104860914A discloses that sulfur pentafluoride phenol is used as a raw material for direct ortho-formylation, and then a benzopyran-based compound is substituted by sulfur pentafluoride, or after multiple steps of synthesis, the ortho position is brominated, and then ortho-formylated, thus a sulfur pentafluoride substituted benzopyran-based compound and a chiral compound thereof are synthesized, it also discloses the synthetic routes of the following sulfur pentafluoride substituted benzopyran-based compounds:

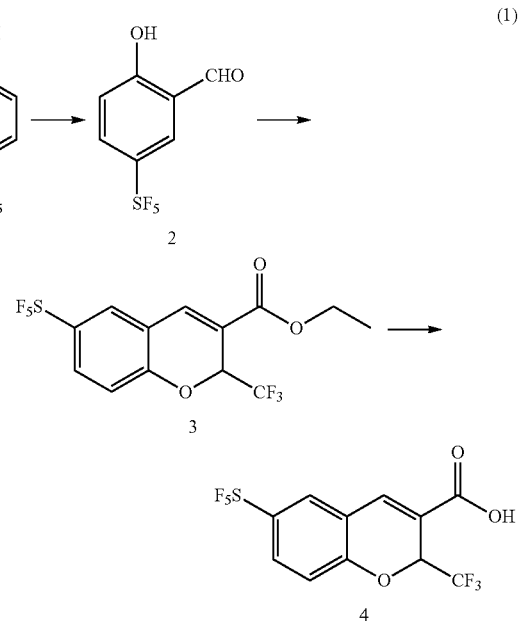

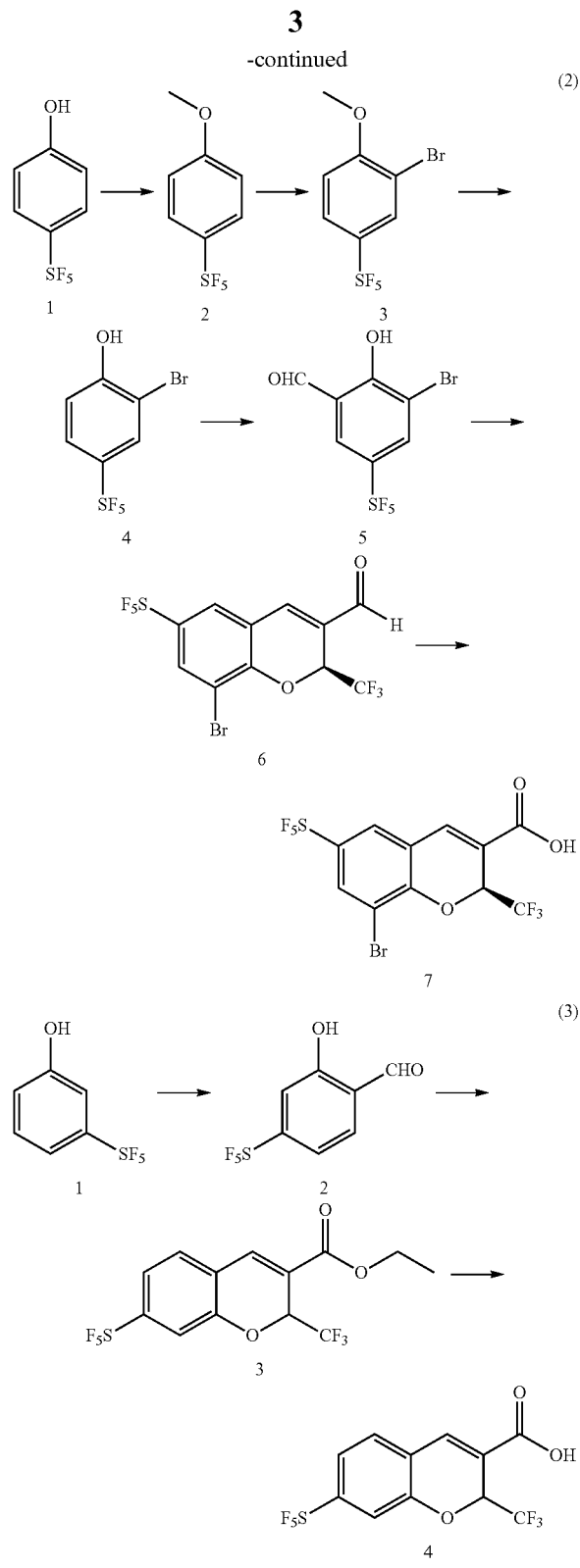

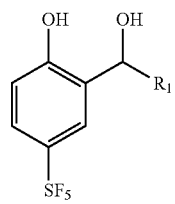

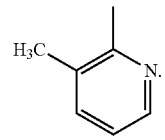

The difficulty in the synthesis of such compounds is that there are very few sulfur pentafluoride phenol-based compounds with substituents in other positions which can satisfy the synthesis conditions and are available. Currently, only sulfur pentafluoride phenol can satisfy the synthesis conditions and is available. The sulfur pentafluoride phenol is needed to be structured to synthesize novel sulfur penta- fluoride phenols with multiple substituent groups, thereby sulfur pentafluoride salicylaldehyde with multiple substituent groups can be obtained. Finally, a sulfur pentafluoride substituted benzopyran-based compound and a chiral structure thereof can be synthesized on this basis.

Therefore, there is still a need in the art to develop a synthetic method for a sulfur pentafluoride substituted benzopyran-based compound.

SUMMARY

The present disclosure provides a 4-sulfur pentafluoride phenol-based compound and a preparation method thereof, and a preparation method for a sulfur pentafluoride substituted benzopyran-based compound.

The present disclosure adopts the following technical solutions:

In one aspect, the present disclosure provides a 4-sulfur pentafluoride phenol-based compound having a structure as shown by formula II below:

Formula II

[Structure showing phenol with OH, SF5 and CH(OH)R1 substituents]

wherein, $R_1$ is any one selected from a group consisting of hydrogen, $C_1$-$C_{10}$ alkyl, $C_6$-$C_{15}$ alkylaryl and $C_3$-$C_8$ heterocyclic radical.

preferably, $R_1$ is any one selected from a group consisting of $C_1$-$C_8$ alkyl, $C_6$-$C_{11}$ alkylaryl and $C_4$-$C_6$ heterocyclic radical.

preferably, $R_1$ is any one selected from a group consisting of methyl, ethyl, propyl, isopropyl, butyl, isobutyl, tert-butyl, pentyl, isopentyl, neopentyl, phenyl, benzyl, substituted benzyl and

[Structure of methylpyridine]

In a second aspect, the present disclosure provides a preparation method for 4-sulfur pentafluoride phenol-based compound as shown by the formula II, and the preparation method comprises the following steps: compound I reacts with sodium borohydride or a Grignard reagent to obtain compound II, as shown by the following reaction formula:

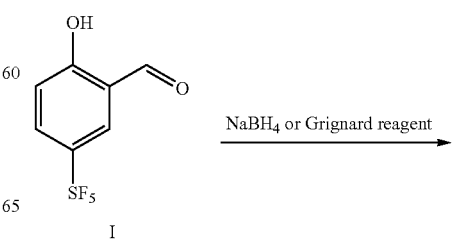

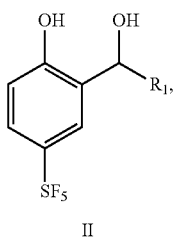

II wherein, $R_1$ is any one selected from a group consisting of hydrogen, $C_1$-$C_{10}$ alkyl, $C_6$-$C_{15}$ alkylaryl and $C_3$-$C_8$ heterocyclic radical;

preferably, the compound I is prepared by using 4-sulfur pentafluoride phenol as a raw material, and the preparation method is as follows: 4-sulfur pentafluoride phenol reacts with hexamethylenetetramine in an acid solution to obtain compound I, as shown by the following reaction formula:

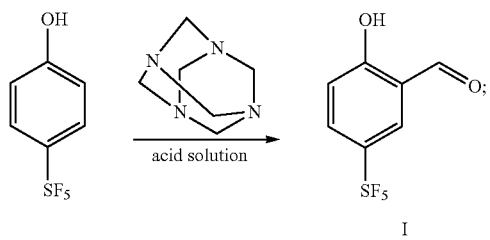

preferably, the acid solution is any one or a combination of at least two selected from a group consisting of polyphosphoric acid, glacial acetic acid and trifluoroacetic acid, preferably trifluoroacetic acid.

Preferably, the molar ratio of 4-sulfur pentafluoride phenol to hexamethylenetetramine is from 1:1.2 to 1:2, for example 1:1.2, 1:1.3, 1:1.4, 1:1.5, 1:1.6, 1:1.7, 1:1.8, 1:1.9 or 1:2, preferably 1:1.5.

Preferably, the acid solution is used in an amount from 5 to 15 mL on the basis of 1 g of 4-sulfur pentafluoride phenol, for example 5 mL, 6 mL, 7 mL, 8 mL, 9 mL, 10 mL, 11 mL, 12 mL, 13 mL, 14 mL or 15 mL.

Preferably, the temperature at which 4-sulfur pentafluoride phenol and hexamethylenetetramine react in an acid solution is from 70° C. to 90° C., for example 70° C., 73° C., 75° C., 78° C., 80° C., 82° C., 85° C., 88° C. or 90° C., preferably 80° C.

Preferably, the time for the reaction between 4-sulfur pentafluoride phenol and hexamethylenetetramine in an acid solution is from 5 to 24 hours, for example 5 hours, 6 hours, 7 hours, 8 hours, 9 hours, 10 hours, 12 hours, 14 hours, 16 hours, 18 hours, 20 hours, 22 hours or 24 hours, preferably from 12 to 18 hours.

In the present disclosure, the Grignard reagent in step (2) has a molecular formula of $R_3MgX$, wherein $R_3$ is any one selected from a group consisting of $C_1$-$C_{10}$ alkyl, $C_6$-$C_{15}$ alkylaryl and $C_3$-$C_8$ heterocyclic radical, and X is a halogen, preferably chlorine or bromine.

Preferably, the Grignard reagent in step (2) is a Methyl Grignard reagent (i.e., $CH_3MgX$) or an Ethyl Grignard reagent (i.e., $CH_3CH_2MgX$), further preferably methyl magnesium bromide or ethyl magnesium bromide.

When compound II is obtained by the reaction between compound I and a Grignard reagent in step (2), $R_1$=$R_2$, that is, $R_1$ group in compound II corresponds to $R_2$ group derived from a Grignard reagent. When compound II is obtained by the reaction between compound I and sodium borohydride in step (2), $R_1$ is hydrogen.

Preferably, the molar ratio of compound I to sodium borohydride or a Grignard reagent is from 1:2 to 1:4, for example 1:2, 1:2.2, 1:2.5, 1:2.8, 1:3, 1:3.2, 1:3.5, 1:3.8 or 1:4, preferably 1:4.

Preferably, the solvent for the reaction between compound I and sodium borohydride or a Grignard reagent is a C1-C4 alcohol, for example methanol, ethanol, isopropanol or butanol, preferably ethanol.

Preferably, the solvent is used in an amount from 10 to 20 mL on the basis of 1 g of compound I, for example 10 mL, 11 mL, 12 mL, 13 mL, 14 mL, 15 mL, 16 mL, 17 mL, 18 mL, 19 mL or 20 mL.

Preferably, the reaction between compound I and sodium borohydride or a Grignard reagent is carried out under a reflux condition.

Preferably, the time for the reaction between compound I and sodium borohydride or a Grignard reagent is from 1 to 5 hours, for example 1 hour, 1.5 hours, 2 hours, 2.5 hours, 3 hours, 3.5 hours, 4 hours, 4.5 hours or 5 hours.

In a third aspect, the present disclosure provides a 4-sulfur pentafluoride phenol-based compound having a structure as shown by the formula III (b) below:

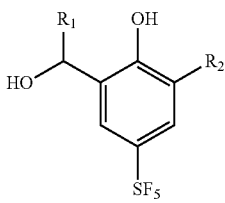

III (b)

wherein, $R_1$ is any one selected from a group consisting of hydrogen, $C_1$-$C_{10}$ alkyl, $C_6$-$C_{15}$ alkylaryl and $C_3$-$C_8$ heterocyclic radical, and $R_2$ is halogen.

preferably, $R_1$ is any one selected from a group consisting of $C_1$-$C_8$ alkyl, $C_6$-$C_{11}$ alkylaryl and $C_4$-$C_6$ heterocyclic radical;

preferably, $R_1$ is any one selected from a group consisting of methyl, ethyl, propyl, isopropyl, butyl, isobutyl, tert-butyl, pentyl, isopentyl, neopentyl, phenyl, benzyl, substituted benzyl and

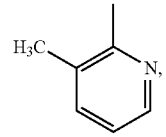

and $R_2$ is selected from a group consisting of F, Br, Cl and I.

In a fourth aspect, the present disclosure provides a preparation method for 4-sulfur pentafluoride phenol-based compound as shown by formula III(b), and the method comprises the following steps: compound II reacts with a halogenated reagent to obtain compound III(b), as shown by the following reaction formula:

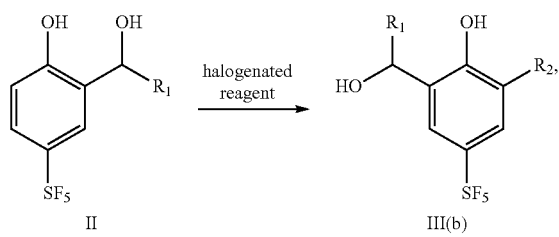

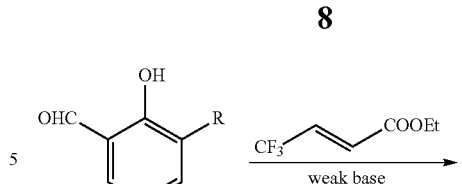

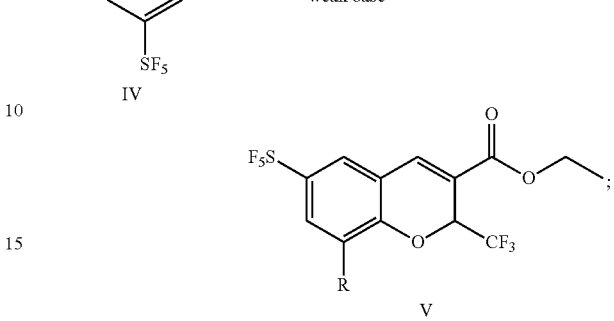

wherein, $R_1$ is any one selected from a group consisting of hydrogen, $C_1$-$C_{10}$ alkyl, $C_6$-$C_{15}$ alkylaryl and $C_3$-$C_8$ heterocyclic radical, and $R_2$ is halogen.

Preferably, the halogenated reagent is N-chlorosuccinimide and/or N-bromosuccinimide.

Preferably, the molar ratio of compound II to a halogenated reagent is from 1:2 to 1:4, for example 1:2, 1:2.2, 1:2.5, 1:2.8, 1:3, 1:3.2, 1:3.4, 1:3.6, 1:3.8 or 1:4.

Preferably, the reaction temperature is from 60° C. to 100° C., for example 60° C., 65° C., 70° C., 75° C., 80° C., 85° C., 90° C., 95° C. or 100° C.

Preferably, the reaction time is from 8 to 24 hours, for example 8 hour, 10 hours, 12 hours, 14 hours, 16 hours, 18 hours, 20 hours, 22 hours or 24 hours.

In the present disclosure, 4-sulfur pentafluoride phenol-based compound as shown by formula II and formula III (b) are two intermediates for preparing a sulfur pentafluoride substituted benzopyran-based compound.

In a fifth aspect, the present disclosure provides a preparation method for a sulfur pentafluoride substituted benzopyran-based compound, and the method comprises the following steps:

(1) Compound II reacts with chloroformate, and then reacts with sodium borohydride to obtain compound III (a), as shown by the following reaction formula:

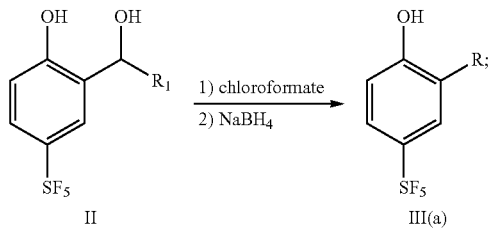

(2) Compound III(a) reacts with hexamethylenetetramine in an acid solution to obtain compound IV, as shown by the following reaction formula:

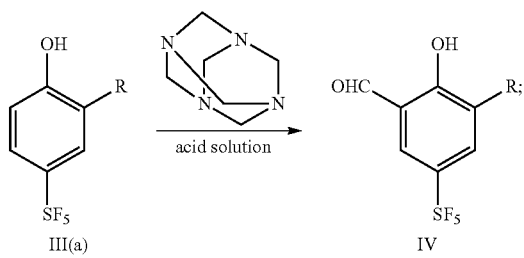

(3) Compound IV reacts with ethyl 4,4,4-trifluorocrotonate and a weak base in a solvent to obtain compound V, as shown by the following reaction formula:

(4) Compound V is hydrolyzed with a base, and then neutralized with an acid to obtain product VI, as shown by the following reaction formula:

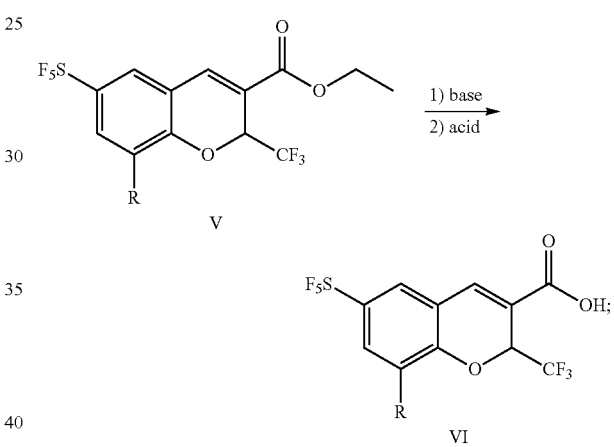

wherein, each of $R_1$ and R is any one independently selected from a group consisting of hydrogen, $C_1$-$C_{10}$ alkyl, $C_6$-$C_{15}$ alkylaryl and $C_3$-$C_8$ heterocyclic radical.

Preferably, each of $R_1$ and R is any one independently selected from a group consisting of $C_1$-$C_8$ alkyl, $C_6$-$C_{11}$ alkylaryl and $C_4$-$C_6$ heterocyclic radical.

Preferably, each of $R_1$ and R is any one independently selected from a group consisting of methyl, ethyl, propyl, isopropyl, butyl, isobutyl, tert-butyl, pentyl, isopentyl, neopentyl, phenyl, benzyl, substituted benzyl and

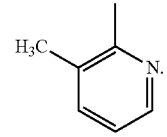

Preferably, the chloroformate in step (1) is any one or a combination of at least two selected from a group consisting of methyl chloroformate, ethyl chloroformate, propyl chloroformate and butyl chloroformate, preferably ethyl chloroformate.

Preferably, the molar ratio of compound II to chloroformate in step (1) is from 1:2 to 1:3, for example 1:2, 1:2.1, 1:2.2, 1:2.3, 1:2.4, 1:2.5, 1:2.6, 1:2.7, 1:2.8, 1:2.9 or 1:3.

Preferably, the molar ratio of compound II to sodium borohydride in step (1) is from 1:8 to 1:10, for example 1:8, 1:8.2, 1:8.4, 1:8.6, 1:8.8, 1:9, 1:9.3, 1:9.5, 1:9.7, 1:9.9 or 1:10.

Preferably, the solvent used in the reaction of compound II with chloroformate in step (1) is dichloromethane and/or chloroform.

Preferably, the reaction of compound II with chloroformate in step (1) is carried out in the presence of a weakly basic substance; preferably, the weakly basic substance is any one or a combination of at least two selected from a group consisting of triethylamine, potassium carbonate, cesium carbonate and cesium fluoride, preferably triethylamine.

Preferably, the molar ratio of compound II to a weakly basic substance is from 1:2 to 1:10, for example 1:2, 1:3, 1:4, 1:5, 1:6, 1:7, 1:8, 1:9 or 1:10, preferably 1:6.

Preferably, the temperature for the reaction between compound II and chloroformate in step (1) is from 0° C. to 30° C., for example 0° C., 3° C., 5° C., 8° C., 10° C., 13° C., 15° C., 18° C., 20° C., 22° C., 25° C., 28° C. or 30° C.

Preferably, the time for the reaction between compound II and chloroformate in step (1) is from 1 to 5 hours, for example 1 hour, 1.3 hours, 1.5 hours, 2 hours, 2.5 hours, 3 hours, 3.5 hours, 4 hours, 4.5 hours or 5 hours.

Preferably, the temperature for the reaction between compound II and sodium borohydride in step (1) is from 0° C. to 30° C., for example 0° C., 3° C., 5° C., 8° C., 10° C., 13° C., 15° C., 18° C., 20° C., 22° C., 25° C., 28° C. or 30° C.

Preferably, the time for the reaction between compound II and sodium borohydride in step (1) is from 1 to 5 hours, for example 1 hour, 1.3 hours, 1.5 hours, 1.8 hours, 2 hours, 2.5 hours, 3 hours, 3.5 hours, 4 hours, 4.5 hours or 5 hours.

Preferably, the acid solution in step (2) is any one or a combination of at least two selected from a group consisting of trifluoroacetic acid, polyphosphoric acid and glacial acetic acid, preferably trifluoroacetic acid.

Preferably, the molar ratio of compound III(a) to hexamethylenetetramine in step (2) is from 1:1.2 to 1:2, for example 1:1.2, 1:1.3, 1:1.4, 1:1.5, 1:1.6, 1:1.7, 1:1.8, 1:1.9 or 1:2, preferably 1:1.7.

Preferably, the amount of the acid solution used in step (4) is from 10 to 30 mL on the basis of 1 g of compound III(a), for example 10 mL, 12 mL, 15 mL, 18 mL, 20 mL, 22 mL, 25 mL, 28 mL or 30 mL.

Preferably, the reaction temperature in step (2) is from 60° C. to 100° C., for example 60° C., 63° C., 65° C., 68° C., 70° C., 73° C., 75° C., 78° C., 80° C., 82° C., 85° C., 88° C., 90° C., 92° C., 95° C., 98° C. or 100° C., preferably 80° C.

Preferably, the reaction time in step (2) is from 8 to 48 hours, for example 8 hours, 10 hours, 12 hours, 15 hours, 18 hours, 20 hours, 22 hours, 24 hours, 26 hours, 28 hours, 30 hours, 33 hours, 36 hours, 38 hours, 40 hours, 44 hours or 48 hours, preferably from 12 to 18 hours.

Preferably, the molar ratio of compound IV to ethyl 4,4,4-trifluorocrotonate in step (3) is from 1:1.2 to 1:10, for example 1:1.2, 1:1.5, 1:1.8, 1:2, 1:2.5, 1:3, 1:3.5, 1:4, 1:4.5, 1:5, 1:6, 1:7, 1:8, 1:9 or 1:10, preferably 1:5.

In the present disclosure, the ethyl 4,4,4-trifluorocrotonate can also be replaced by methyl 4,4,4-trifluorocrotonate, and likewise the product VI of the present disclosure can be obtained.

Preferably, the weak base in step (3) is any one or a combination of at least two selected from a group consisting of triethylamine, potassium carbonate, cesium carbonate and cesium fluoride, preferably triethylamine.

Preferably, the amount of the weak base used in step (3) is from 10 to 20 mL on the basis of 1 g of compound IV, for example 10 mL, 11 mL, 12 mL, 13 mL, 14 mL, 15 mL, 16 mL, 18 mL, 19 mL or 20 mL.

Preferably, the solvent in step (3) is any one or a combination of at least two selected from a group consisting of triethylamine, tetrahydrofuran, N,N-dimethylformamide and dimethyl sulfoxide. In the present disclosure, triethylamine can be used as a reaction solvent, which can not only provide an alkaline environment as a weakly basic substance, but also serve as a solvent for the reaction.

Preferably, the reaction temperature in step (3) is from 80 to 120° C., for example 80° C., 83° C., 85° C., 88° C., 90° C., 93° C., 95° C., 98° C., 100° C., 103° C., 105° C., 108° C., 110° C., 112° C., 115° C., 118° C. or 120° C.

Preferably, the reaction time in step (3) is from 10 to 72 hours, for example 10 hours, 12 hours, 14 hours, 16 hours, 18 hours, 20 hours, 22 hours, 24 hours, 28 hours, 30 hours, 36 hours, 40 hours, 44 hours, 48 hours, 52 hours, 56 hours, 60 hours, 65 hours, 68 hours or 72 hours, preferably from 12 to 20 hours.

Preferably, the base in step (4) is any one or a combination of at least two selected from a group consisting of potassium hydroxide, sodium hydroxide and lithium hydroxide.

Preferably, the molar ratio of compound V to the base in step (4) is from 1:10 to 1:20, for example 1:10, 1:11, 1:12, 1:13, 1:14, 1:15, 1:16, 1:17, 1:18, 1:19 or 1:20.

Preferably, the temperature for the hydrolysis with a base in step (4) is from 20° C. to 30° C., for example 20° C., 21° C., 22° C., 23° C., 24° C., 25° C., 26° C., 27° C., 28° C., 29° C. or 30° C.

Preferably, the time for the hydrolysis with a base in step (4) is from 1 to 5 hours, for example 1 hour, 1.5 hours, 2 hours, 2.5 hours, 3 hours, 3.5 hours, 4 hours, 4.5 hours or 5 hours.

Preferably, the acid in step (4) is hydrochloric acid and/or sulfuric acid.

As a preferred technical solution of the present disclosure, a preparation method for a sulfur pentafluoride substituted benzopyran-based compound specifically comprises the following steps:

(1) 4-sulfur pentafluoride phenol reacts with hexamethylenetetramine in trifluoroacetic acid to obtain compound I, as shown by the following reaction formula:

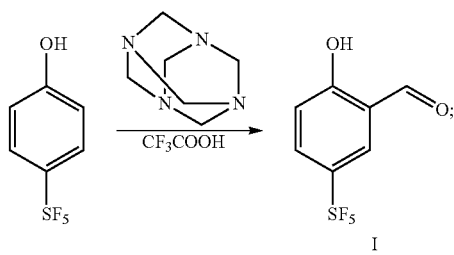

(2) compound I reacts with sodium borohydride or a Grignard reagent to obtain compound II, as shown by the following reaction formula:

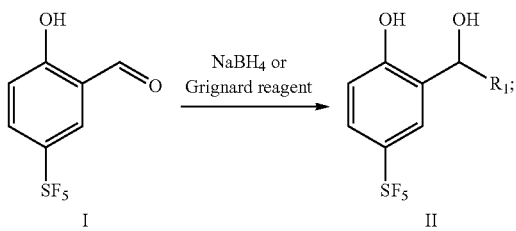

(3) Compound II reacts with ethyl chloroformate in the presence of triethylamine, and then reacts with sodium borohydride to obtain compound III (a), as shown by the following reaction formula:

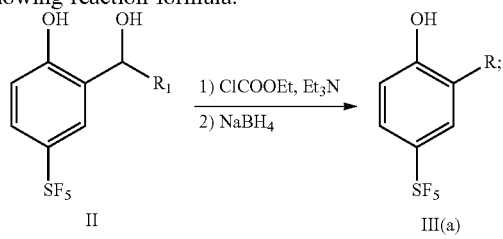

(4) Compound III (a) reacts with hexamethylenetetramine in trifluoroacetic acid to obtain compound IV, as shown by the following reaction formula:

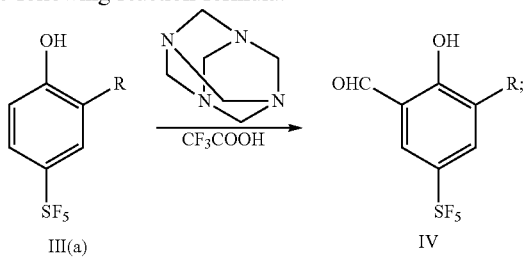

(5) Compound IV reacts with ethyl 4,4,4-trifluorocrotonate and triethylamine in a solvent to obtain compound V, as shown by the following reaction formula:

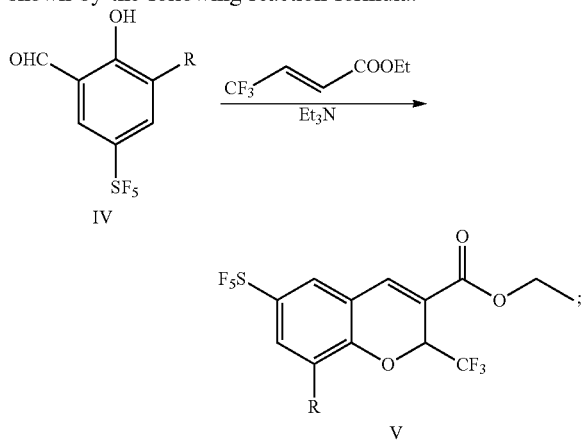

(6) Compound V is hydrolyzed with a base, and then neutralized with an acid to obtain product VI, as shown by the following reaction formula:

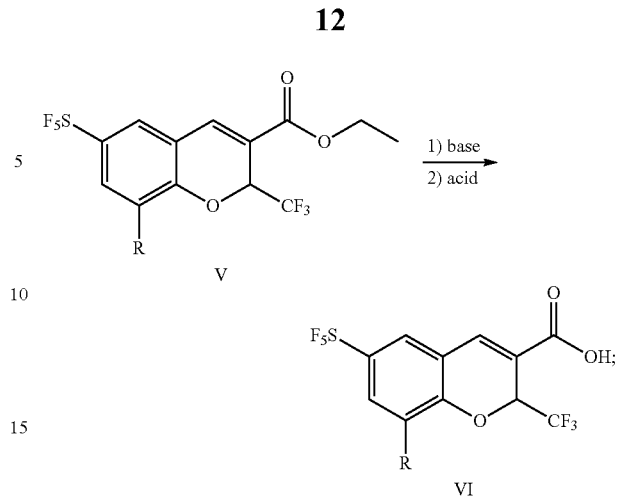

wherein, each of $R_1$ and R is any one independently selected from a group consisting of hydrogen, $C_1$-$C_{10}$ alkyl, $C_6$-$C_{15}$ alkylaryl and $C_3$-$C_8$ heterocyclic radical.

The product VI obtained from this preparation method is a racemate compound, and in order to obtain a chiral compound thereof, a chiral catalyst can be added to the reaction of compound IV with ethyl 4,4,4-trifluorocrotonate.

Preferably, the chiral catalyst is a diphenylprolinol silyl ether-based compound or a dinaphthylprolinol silyl ether-based compound; further preferably, the chiral catalyst is (2S)-2-[diphenyl[(trimethylsilyl)oxy]methyl]-pyrrolidine or (2R)-2-[diphenyl[(trimethylsilyl)oxy]methyl]-pyrrolidine.

Preferably, the molar ratio of the chiral catalyst to compound IV is from 1:4 to 1:6, for example 1:4.2, 1:4.4, 1:4.6, 1:4.8, 1:5, 1:5.2, 1:5.5, 1:5.8 or 1:6, preferably 1:5.

In a sixth aspect, the present disclosure provides another preparation method for a sulfur pentafluoride substituted benzopyran-based compound, in which the product IV(b) is prepared by the intermediate compound III(b), and the preparation method comprises the following steps:

A. compound III (b) reacts with an oxidant to obtain compound IV (b), as shown by the following reaction formula:

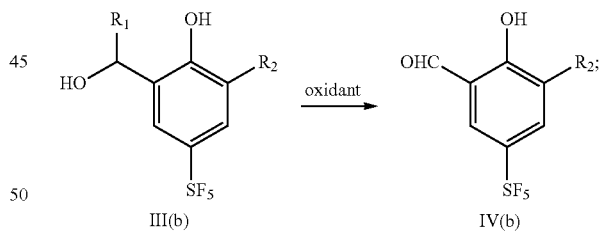

B. Compound IV (b) reacts with ethyl 4,4,4-trifluorocrotonate and a weak base in a solvent to obtain compound V(b), as shown by the following reaction formula:

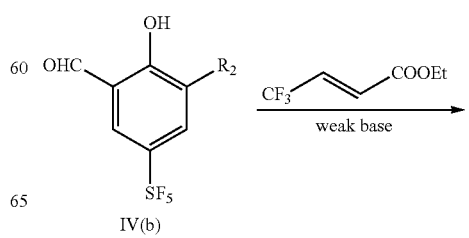

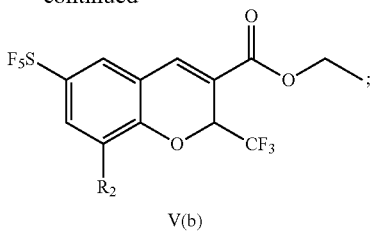

V(b)

C. Compound V (b) is hydrolyzed with a base, and then neutralized with an acid to obtain the product VI (b), as shown by the following reaction formula:

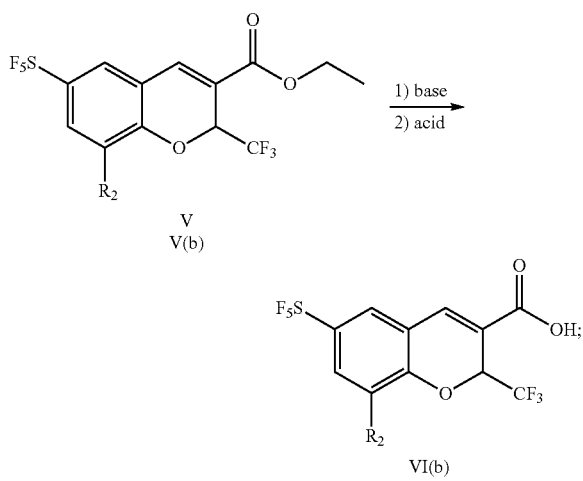

wherein, $R_1$ is any one selected from a group consisting of hydrogen, $C_1$-$C_{10}$ alkyl, $C_6$-$C_{15}$ alkylaryl and $C_3$-$C_8$ heterocyclic radical, and $R_2$ is halogen.

Preferably, the oxidant in step A is pyridinium chlorochromate and/or manganese dioxide.

Preferably, the molar ratio of compound III (b) to the oxidant in step A is from 1:2 to 1:20, for example 1:2, 1:3, 1:4, 1:5, 1:6, 1:7, 1:8, 1:9, 1:10, 1:11, 1:12, 1:13, 1:14, 1:15, 1:16, 1:17, 1:18, 1:19 or 1:20.

Preferably, the reaction temperature in step A is from 10° C. to 30° C., for example 10° C., 12° C., 15° C., 18° C., 20° C., 22° C., 25° C., 27° C. or 30° C.

Preferably, the reaction time in step A is from 5 to 24 hours, for example 5 hours, 8 hours, 10 hours, 12 hours, 14 hours, 16 hours, 18 hours, 20 hours, 22 hours or 24 hours.

Preferably, the molar ratio of compound IV(b) to ethyl 4,4,4-trifluorocrotonate in step B is from 1:1.2 to 1:10, for example 1:1.2, 1:1.5, 1:1.8, 1:2, 1:2.5, 1:3, 1:3.5, 1:4, 1:4.5, 1:5, 1:6, 1:7, 1:8, 1:9 or 1:10, preferably 1:5.

Preferably, the weak base in step B is any one or a combination of at least two selected from a group consisting of triethylamine, potassium carbonate, cesium carbonate and cesium fluoride, preferably triethylamine.

Preferably, the amount of the weak base used in step B is from 10 to 20 mL on the basis of 1 g of compound IV(b), for example 10 mL, 11 mL, 12 mL, 13 mL, 14 mL, 15 mL, 16 mL, 18 mL, 19 mL or 20 mL.

Preferably, the solvent in step B is any one or a combination of at least two selected from a group consisting of triethylamine, tetrahydrofuran, N, N-dimethylformamide and dimethyl sulfoxide.

Preferably, the reaction temperature in step B is from 80 to 120° C., for example 80° C., 83° C., 85° C., 88° C., 90° C., 93° C., 95° C., 98° C., 100° C., 103° C., 105° C., 108° C., 110° C., 112° C., 115° C., 118° C. or 120° C.

Preferably, the reaction time in step B is from 10 to 72 hours, for example 10 hours, 12 hours, 14 hours, 16 hours, 18 hours, 20 hours, 22 hours, 24 hours, 28 hours, 30 hours, 36 hours, 40 hours, 44 hours, 48 hours, 52 hours, 56 hours, 60 hours, 65 hours, 68 hours or 72 hours, preferably from 12 to 20 hours.

Preferably, the base in step C is any one or a combination of at least two selected from a group consisting of potassium hydroxide, sodium hydroxide and lithium hydroxide.

Preferably, the molar ratio of compound V(b) to the base in step C is from 1:10 to 1:20, for example 1:10, 1:11, 1:12, 1:13, 1:14, 1:15, 1:16, 1:17, 1:18, 1:19 or 1:20.

Preferably, the temperature for the hydrolysis with a base in step C is from 20° C. to 30° C., for example 20° C., 21° C., 22° C., 23° C., 24° C., 25° C., 26° C., 27° C., 28° C., 29° C. or 30° C.

Preferably, the time for the hydrolysis with a base in step C is from 1 to 5 hours, for example 1 hour, 1.5 hours, 2 hours, 2.5 hours, 3 hours, 3.5 hours, 4 hours, 4.5 hours or 5 hours.

Preferably, the acid in step C is hydrochloric acid and/or sulfuric acid.

As a preferred technical solution of the present disclosure, a preparation method for a sulfur pentafluoride substituted benzopyran-based compound as described in the sixth aspect of the present disclosure specifically comprises the following steps:

(1) 4-sulfur pentafluoride phenol reacts with hexamethylenetetramine in an acid solution to obtain compound I, as shown by the following reaction formula:

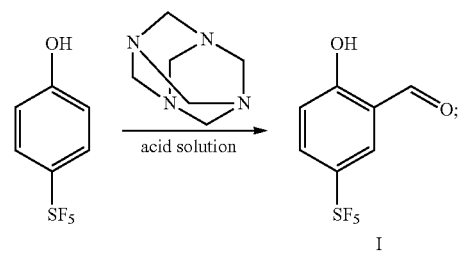

(2) compound I reacts with sodium borohydride or a Grignard reagent to obtain compound II, as shown by the following reaction formula:

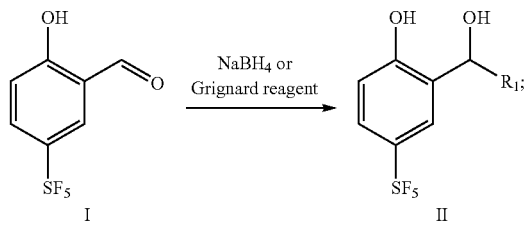

(3) Compound II reacts with a halogenated reagent to obtain compound III (b), as shown by the following reaction formula:

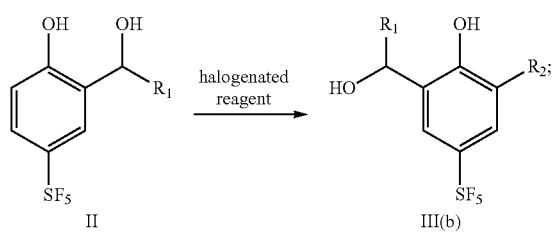

(4) compound III(b) reacts with an oxidant to obtain compound IV, as shown by the following reaction formula:

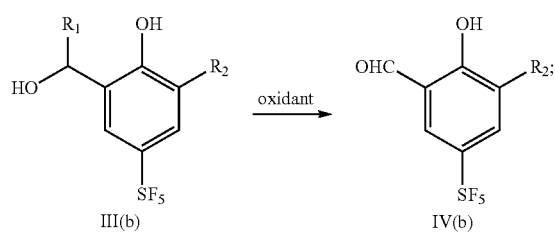

(5) Compound IV reacts with ethyl 4,4,4-trifluorocrotonate and a weak base in a solvent to obtain compound V, as shown by the following reaction formula:

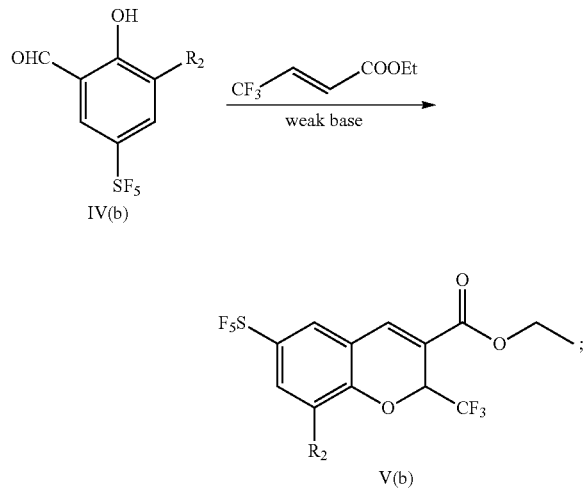

(6) Compound V (b) is hydrolyzed with a base, and then neutralized with an acid to obtain product VI (b), as shown by the following reaction formula:

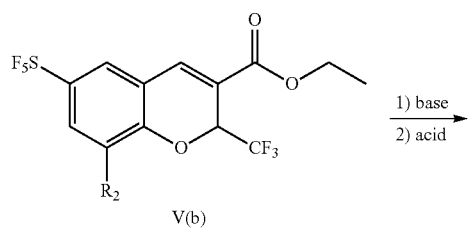

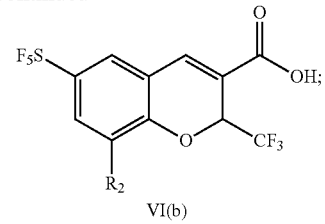

wherein, $R_1$ is any one selected from a group consisting of hydrogen, $C_1$-$C_{10}$ alkyl, $C_6$-$C_{15}$ alkylaryl and $C_3$-$C_8$ heterocyclic radical, and $R_2$ is halogen.

preferably, $R_1$ is any one selected from a group consisting of $C_1$-$C_{10}$ alkyl, $C_6$-$C_{11}$ alkylaryl and $C_4$-$C_6$ heterocyclic radical.

preferably, $R_1$ is any one selected from a group consisting of methyl, ethyl, propyl, isopropyl, butyl, isobutyl, tert-butyl, pentyl, isopentyl, neopentyl, phenyl, benzyl, substituted benzyl and

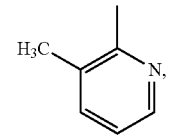

and $R_2$ is selected from a group consisting of F, Br, Cl and I.

Same as the preparation method of the fifth aspect of the present disclosure, the product VI obtained from this preparation method is also a racemate compound, and in order to obtain a chiral compound thereof, a chiral catalyst can be added to the reaction of compound IV(b) with ethyl 4,4,4-trifluorocrotonate.

Preferably, the chiral catalyst is a diphenylprolinol silyl ether-based compound or a dinaphthylprolinol silyl ether-based compound; further preferably, the chiral catalyst is (2S)-2-[diphenyl[(trimethylsilyl)oxy]methyl]-pyrrolidine or (2R)-2-[diphenyl[(trimethylsilyl)oxy]methyl]-pyrrolidine.

Preferably, the molar ratio of the chiral catalyst to compound IV(b) is from 1:4 to 1:6, for example 1:4.2, 1:4.4, 1:4.6, 1:4.8, 1:5, 1:5.2, 1:5.5, 1:5.8 or 1:6, preferably 1:5.

In the present disclosure, both in the description of the structure of the product or in the description of the preparation method, $C_1$-$C_{10}$ (for example, $C_1$, $C_2$, $C_3$, $C_4$, $C_5$, $C_6$, $C_7$, $C_8$, $C_9$ or $C_{10}$) alkyl group can be methyl, ethyl, n-propyl, isopropyl, n-butyl, isobutyl, n-pentyl, isopentyl, neopentyl, n-hexyl, n-heptyl, n-octyl, n-nonyl, n-decyl, and the like, preferably $C_1$-$C_5$ alkyl; the $C_6$-$C_{15}$ alkylaryl refers to an alkylaryl group containing 6 to 15 carbon atoms, for example it can be $C_6$, $C_7$, $C_8$, $C_9$, $C_{10}$, $C_{11}$, $C_{12}$, $C_{13}$, $C_{14}$ or $C_{15}$ alkylaryl, for example specifically can be phenyl, benzyl, substituted benzyl, ethylphenyl, propylphenyl, pentylphenyl, hexylphenyl, heptylphenyl, octylphenyl, nonylphenyl, and the like; the $C_3$-$C_8$ heterocyclic radical refers to a heterocyclic group containing 3 to 8 carbon atoms, for example it can be $C_3$, $C_4$, $C_5$, $C_6$, $C_7$ or $C_8$ heterocyclic radical, preferably pyridyl or furyl; and the halogen is fluorine, chlorine, bromine or iodine, preferably chlorine or bromine.

Compared with the related technics, the present disclosure has the following beneficial effects:

By means of the preparation method of the present disclosure, various sulfur pentafluoride substituted benzopyran-based compounds can be synthesized, which overcomes the defects that, at present, the type of sulfur pentafluoride phenol is less, and the need for synthesis of various sulfur pentafluoride substituted benzopyran-based compounds cannot be met. The preparation method of the present disclosure can realize the synthesis of various sulfur pentafluoride phenol intermediates with multiple substituent groups by using relatively inexpensive raw materials under mild conditions, thereby realizing the synthesis of sulfur pentafluoride substituted benzopyran-based compound.

DETAILED DESCRIPTION

The technical solutions of the present disclosure will be further described below by way of specific embodiments. It will be apparent to those skilled in the art that the embodiments are merely illustrations of the present disclosure and should not be construed as specific limitations to the present disclosure.

Example 1 Synthesis of 6-sulfur pentafluoride-8-methyl-2-trifluoromethyl-2H-benzopyran-3-carboxylic acid The synthetic route is as follows:

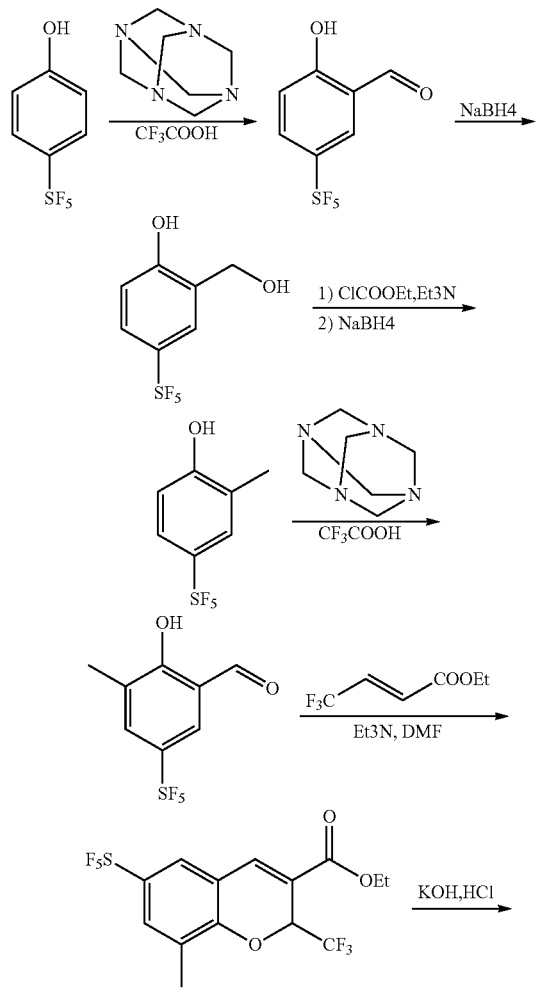

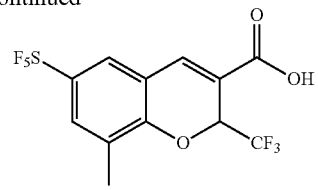

(1) Synthesis of 5-sulfur pentafluoride-2-hydroxybenzaldehyde

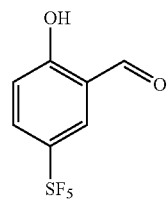

Under protection of argon, p-sulfur pentafluoride phenol (1.0 g, 4.5 mmol) was dissolved in trifluoroacetic acid (6 mL), and then hexamethylenetetramine (1.0 g, 7.1 mmol) was slowly added to the above solution, the reaction was maintained at a temperature of 80° C. for 12 h, the reaction solution was cooled to room temperature, to which 6 mL of hydrochloric acid (3 mol/L) was added and then stirred for another 0.5 h. After the reaction was completed, the reaction solution was extracted with ethyl acetate, and the resulting organic phase was washed with brine, dried, and rotary evaporated under reduced pressure, then purified through column chromatography to give the product (0.53 g, 47%).

$^1$H NMR (400 MHz, CDCl$_3$) δ 11.31 (s, 1H), 9.94 (s, 1H), 7.99 (d, J=2.7 Hz, 1H), 7.90 (dd, J=9.2, 2.7 Hz, 1H), 7.02 (dd, J=35.3, 11.0 Hz, 1H). MS (MM−ES+APCI), m/z: 247.0 (M-H$^+$).

(2) Synthesis of 4-sulfur pentafluoride-2-hydroxymethylphenol

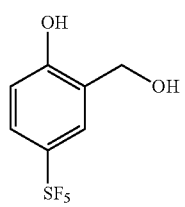

5-sulfur pentafluoride-2-hydroxybenzaldehyde (0.40 g, 1.61 mmol) and ethanol (6 mL) were added to a single-necked flask, to which solid sodium borohydride (0.080 g, 2.2 mmol) was slowly added, the mixture was heated to reflux for 2 h, then cooled to room temperature and adjusted to a pH of less than 3 with hydrochloric acid (3 mol/L), which was then extracted three times with dichloromethane (20 mL), the resulting organic phase was washed with brine, dried over anhydrous sodium sulfate for 15 minutes and directly used for the next reaction.

$^1$H NMR (400 MHz, CDCl$_3$) δ 10.559 (s, 1H), 7.75 (s, 1H), 7.57 (d, J=8 Hz, 1H), 6.88 (dd, J=8 Hz, 1H), 4.49 (s, 2H).

(3) Synthesis of 4-sulfur pentafluoride-2-methylphenol

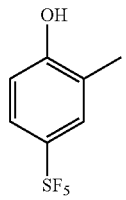

Under protection of argon, the dichloromethane solution containing crude product (theoretical value 0.40 g, 1.61 mmol) obtained in step 2 was cooled in an ice bath, to which triethylamine (9.6 mmol, 1.05 g) was added, subsequently ethyl chloroformate (0.52 g, 4.80 mmol) was added dropwise, the mixture was stirred for 30 minutes, then warmed to room temperature and stirred for 1.5 h. At the end of the reaction, the solvent was distilled off under reduced pressure to give a solid residue, which was dissolved in ethanol (3 mL), and slowly added dropwise to an aqueous solution (5 mL) of sodium borohydride (1.5 g, 38.4 mmol) in ice bath, then the mixture was stirred for 0.5 h, and warmed to room temperature and stirred for 1.5 h.

After the reaction was completed, the mixture was adjusted to a pH of less than 3 by carefully adding dropwise dilute hydrochloric acid (3 mol/L) in ice bath, then extracted with dichloromethane, dried over anhydrous sodium sulfate, and the solvent was distilled off under reduced pressure, the crude product was isolated by column chromatography to give the product (0.30 g, 1.3 mmol, 80%).

$^1$H NMR (400 MHz, CDCl$_3$) δ 7.53 (t, J=5.8 Hz, 1H), 7.46 (dd, J=8.8, 2.7 Hz, 1H), 6.79 (d, J=8.8 Hz, 1H), 2.28 (s, 3H). MS (MM−ES+APCI), m/z: 233 (M-H$^+$).

(4) Synthesis of 5-sulfur pentafluoride-2-hydroxy-3-methylbenzaldehyde

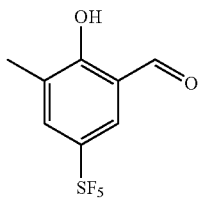

Under protection of argon, the resulting product 4-sulfur pentafluoride-2-methylphenol (0.30 g, 1.3 mmol) obtained in step 3 was dissolved in trifluoroacetic acid (6 mL), and then hexamethylenetetramine (0.31 g, 2.22 mmol) was slowly added to the above solution, the reaction was maintained at a temperature of 80° C. for 12 h, and then the reaction solution was cooled to room temperature, to which 3 mL of hydrochloric acid (3 mol/L) was added and then stirred for another 0.5 h. After the reaction was completed, the reaction solution was extracted with ethyl acetate, and the resulting organic phase was washed with brine, dried, and rotary evaporated under reduced pressure, then purified through column chromatography to give the product (0.16 g, 0.61 mmol, 47%).

$^1$H NMR (400 MHz, CDCl$_3$) δ 11.56 (s, 1H), 9.91 (s, 1H), 7.83 (d, J=2.5 Hz, 1H), 7.76 (s, 1H), 2.33 (s, 3H).

MS (MM−ES+APCI), m/z: 261.0 (M-H$^+$).

(5) Synthesis of Ethyl 6-sulfur pentafluoride-8-methyl-2-trifluoromethyl-2H-benzopyran-3-carboxylate

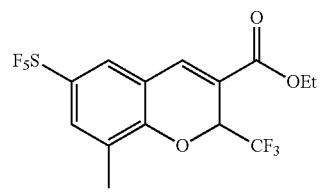

5-sulfur pentafluoride-2-hydroxy-3-methylbenzaldehyde (0.16 g, 0.61 mmol), ethyl 4,4,4-trifluorocrotonate (0.50 g, 3.0 mmol), and triethylamine (2 mL) were dissolved in DMF (5 ml), then stirred in a sealed tube at 110° C. for 12 h. After the reaction was completed, the reaction solution was cooled to room temperature and adjusted to a pH of less than 3 with hydrochloric acid (3 mol/L), then extracted with ethyl acetate, and the resulting organic phase was dried, and rotary evaporated under reduced pressure, then purified through column chromatography to give the product (0.12 g, 0.29 mmol, 48%).

$^1$H NMR (400 MHz, CDCl$_3$) δ 7.70 (s, 1H), 7.56 (d, J=2.3 Hz, 1H), 7.48 (d, J=2.5 Hz, 1H), 5.81 (q, J=6.7 Hz, 1H), 4.41-4.26 (m, 2H), 2.31 (s, 3H), 1.35 (dd, J=12.6, 5.4 Hz, 3H).

MS (MM−ES+APCI), m/z: 411 (M-H$^+$).

(6) Synthesis of 6-sulfur pentafluoride-8-methyl-2-trifluoromethyl-2H-benzopyran-3-carboxylic acid

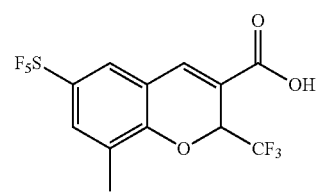

The product obtained in step 5 (0.12 g, 0.29 mmol), potassium hydroxide (0.16 g, 2.9 mmol), ethanol (3 ml), and water (1 ml) were added in sequence to a single-necked flask. The mixture was stirred at room temperature for 3 h, the pH was adjusted to less than 3 after the completion of the reaction, which was then extracted with ethyl acetate, washed with saturated sodium chloride aqueous solution, dried and rotary evaporated under reduced pressure to give the product (0.10 g, 0.26 mmol, 90%).

$^1$H NMR (400 MHz, CDCl$_3$) δ 7.81 (s, 1H), 7.60 (d, J=2.1 Hz, 1H), 7.51 (d, J=2.5 Hz, 1H), 5.80 (q, J=6.6 Hz, 1H), 2.31 (s, 3H).

MS (MM−ES+APCI), m/z: 383.0 (M-H$^+$).

Example 2 Synthesis of 6-sulfur pentafluoride-8-ethyl-2-trifluoromethyl-2H-benzopyran-3-carboxylic acid The synthetic route is as follows:

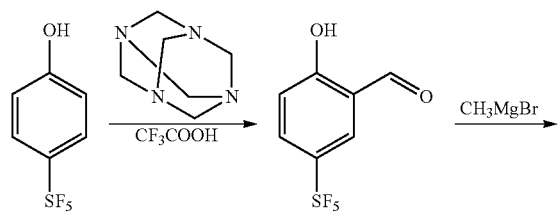

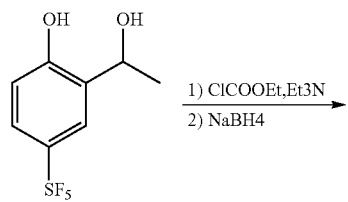

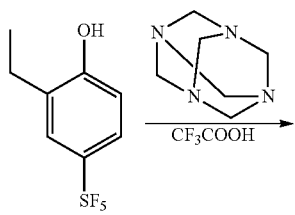

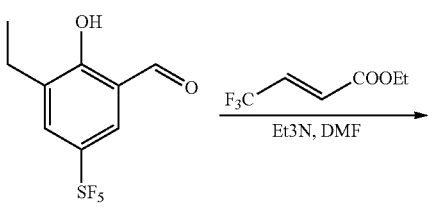

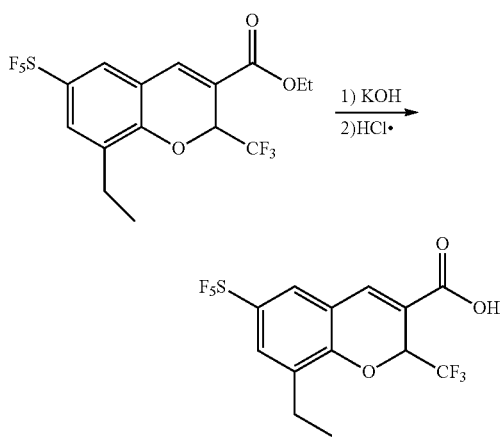

(1) Synthesis of 5-sulfur pentafluoride-2-hydroxybenzaldehyde

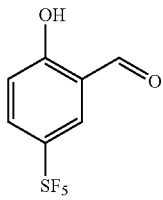

The p-sulfur pentafluoride phenol (1.0 g, 4.5 mmol) was dissolved in trifluoroacetic acid (6 mL), and then hexamethylenetetramine (1.0 g, 7.1 mmol) was slowly added to the above solution, the reaction was maintained at a temperature of 80° C. for 12 h, the reaction solution was cooled to room temperature, to which 6 mL of hydrochloric acid (3 mol/L) was added and then stirred for another 0.5 h. After the reaction was completed, the reaction solution was extracted with ethyl acetate, and the resulting organic phase was washed with brine, dried, and rotary evaporated under reduced pressure, then purified through column chromatography to give the product (0.53 g, 2.4 mmol, 47%).

$^1$H NMR (400 MHz, CDCl$_3$) δ 11.31 (s, 1H), 9.94 (s, 1H), 7.99 (d, J=2.7 Hz, 1H), 7.90 (dd, J=9.2, 2.7 Hz, 1H), 7.02 (dd, J=35.3, 11.0 Hz, 1H).

MS (MM–ES+APCI), m/z: 247.0 (M-H$^+$).

(2) Synthesis of 4-sulfur pentafluoride-2-(1-hydroxyethyl)phenol

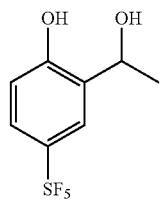

Under protection of argon, 5-sulfur pentafluoride-2-hydroxybenzaldehyde (0.53 g, 2.4 mmol), and dry tetrahydrofuran (6 mL) were added to a two-necked flask, methyl magnesium bromide (3.7 mL, 4.8 mmol, 1.3 mol/L solution) was slowly added at room temperature, and the reaction was stirred overnight. After the reaction was completed, the reaction mixture was adjusted to a pH of less than 3 with hydrochloric acid (3 mol/L), and extracted three times with ethyl acetate (20 mL), the organic phase was washed with brine, dried over anhydrous sodium sulfate, and the solvent was distilled off under reduced pressure to give the product (0.52 g, 2.0 mmol, 81%).

$^1$H NMR (400 MHz, CDCl$_3$) δ 8.60 (s, 1H), 7.56 (dd, J=8.9, 2.6 Hz, 1H), 7.38 (d, J=2.5 Hz, 1H), 6.89 (d, J=9.0 Hz, 1H), 5.12 (q, J=6.5 Hz, 1H), 1.61 (d, J=6.6 Hz, 3H). MS (MM–ES+APCI), m/z: 263.0 (M-H$^+$).

(3) Synthesis of 4-sulfur pentafluoride-2-ethylphenol

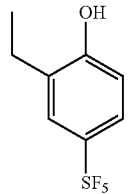

Under protection of argon, the product (0.52 g, 2.0 mmol) obtained in step 2 was dissolved in dichloromethane (5 mL), the solution was cooled in an ice bath, to which triethylamine (12 mmol, 12.20 g) was added, subsequently ethyl chloroformate (0.65 g, 6 mmol) was added dropwise, the mixture was stirred for 30 minutes, then warmed to room temperature and stirred for 3 h. At the end of the reaction, the solvent was distilled off under reduced pressure to give a solid residue, which was dissolved in ethanol (10 mL), and slowly added dropwise to an aqueous solution (20 mL) of sodium borohydride (1.82 g, 48 mmol), then the mixture was stirred for 0.5 h, and warmed to room temperature and stirred overnight.

After the reaction was completed, the mixture was adjusted to a pH of less than 3 by carefully adding dropwise dilute hydrochloric acid (3 mol/L) in an ice bath, then extracted with dichloromethane, the organic phase was dried over anhydrous sodium sulfate, and the solvent was distilled off under reduced pressure, the crude product was directly used for the next reaction.

MS (MM−ES+APCI), m/z: 247.0 (M-H$^+$).

(4) Synthesis of 5-sulfur pentafluoride-2-hydroxy-3-ethylbenzaldehyde

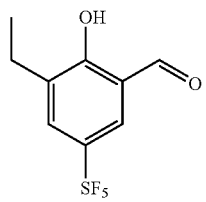

Under protection of argon, the crude product 4-sulfur pentafluoride-2-ethyl-phenol (Theoretical content 0.48 g, 2.0 mmol) obtained in step 3 was dissolved in trifluoroacetic acid (6 mL), and then hexamethylenetetramine (0.440 g, 3.14 mmol) was slowly added to the above solution, the reaction was maintained at a temperature of 80° C. for 12 h, the reaction solution was cooled to room temperature, to which 12 mL of hydrochloric acid (3 mol/L) was added and then stirred for another 0.5 h. After the reaction was completed, the reaction solution was extracted with ethyl acetate, and the resulting organic phase was washed with brine, dried, and rotary evaporated under reduced pressure, then purified through column chromatography to give the product (0.160 g, 0.56 mmol, 28%).

$^1$H NMR (400 MHz, CDCl$_3$) δ 11.58 (s, 1H), 9.91 (s, 1H), 7.83 (d, J=2.7 Hz, 1H), 7.76 (d, J=2.6 Hz, 1H), 2.75 (q, J=7.5 Hz, 2H), 1.30-1.22 (m, 3H). MS (MM−ES+APCI), m/z: 275.0 (M-H$^+$).

(5) Synthesis of Ethyl 6-sulfur pentafluoride-8-ethyl-2-trifluoromethyl-2H-benzopyran-3-carboxylate

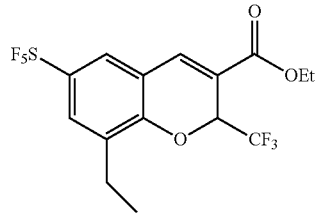

5-sulfur pentafluoride-2-hydroxy-3-ethylbenzaldehyde (0.160 g, 0.56 mmol), ethyl 4,4,4-trifluorocrotonate (0.47 g, 2.80 mmol), and triethylamine (2 mL) were dissolved in DMF (5 ml), then stirred in a sealed tube at 110° C. overnight. After the reaction was completed, the reaction solution was cooled to room temperature and adjusted to a pH of less than 3 with hydrochloric acid (3 mol/L), then extracted with ethyl acetate, and the resulting organic phase was dried, and rotary evaporated under reduced pressure, then purified through column chromatography to give the product (0.12 g, 0.28 mmol, 50%).

$^1$H NMR (400 MHz, CDCl$_3$) δ 7.70 (s, 1H), 7.56 (d, J=2.6 Hz, 1H), 7.49 (d, J=2.6 Hz, 1H), 5.82 (q, J=6.7 Hz, 1H), 4.40-4.26 (m, 2H), 2.81-2.58 (m, 2H), 1.36 (t, J=7.1 Hz, 3H), 1.28-1.18 (t, J=7.2 Hz, 3H). MS (MM−ES+APCI), m/z: 425.0 (M-H$^+$).

(6) Synthesis of 6-sulfur pentafluoride-8-ethyl-2-trifluoromethyl-2H-benzopyran-3-carboxylic acid

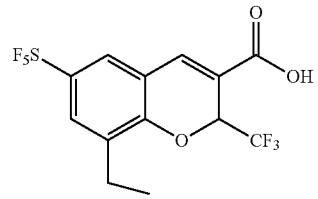

The product obtained in step 5 (0.12 g, 0.28 mmol), potassium hydroxide (0.16 g, 2.8 mmol), ethanol (12 ml), and water (4 ml) were added in sequence to a single-necked flask. The mixture was stirred at room temperature for 3 h, the pH was adjusted to less than 3 after the completion of the reaction, which was then extracted with ethyl acetate, washed with saturated sodium chloride aqueous solution, dried and rotary evaporated under reduced pressure to give the product (0.080 g, 0.20 mmol, 70%).

$^1$H NMR (400 MHz, CDCl$_3$) δ 7.82 (s, 1H), 7.60 (d, J=2.6 Hz, 1H), 7.52 (d, J=2.5 Hz, 1H), 5.80 (q, J=6.6 Hz, 1H), 2.71 (ddd, J=30.8, 14.5, 7.3 Hz, 2H), 1.36-1.17 (m, 3H). MS (MM−ES+APCI), m/z: 397.0 (M-H$^+$).

Example 3 Synthesis of 6-sulfur pentafluoride-8-propyl-2-trifluoromethyl-2H-benzopyran-3-carboxylic acid The synthesis method in this Example differs from that in Example 2 only in that the Grignard reagent used in step (2) is ethyl magnesium bromide, which is used in a molar ratio of 4:1 to 5-sulfur pentafluoride-2-hydroxybenzaldehyde. In addition, the preparation methods and conditions are the same as those in Example 2, and by characterization via 1H NMR spectroscopy and mass spectrometry, 6-sulfur pentafluoride-8-propyl-2-trifluoromethyl-2H-benzopyran-3-carboxylic acid is determined to have the following structure:

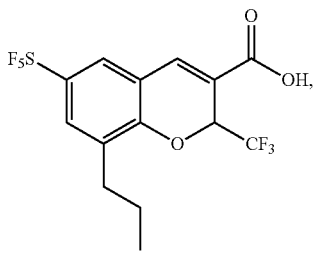

The characterization results of 1H NMR spectroscopy and mass spectrometry are as follows: $^1$H NMR (400 MHz, CDCl$_3$) δ 7.82 (s, 1H), 7.58 (d, J=2.6 Hz, 1H), 7.51 (s, J=2.6 Hz, 1H), 5.79 (q, J=6.7 Hz, 1H), 2.78-2.54 (m, 2H), 1.71-1.57 (m, 2H), 0.97 (t, J=7.4 Hz, 3H). MS (MM−ES+APCI), m/z: 411.0 (M-H$^+$).

Example 4 Synthesis of 6-sulfur pentafluoride-8-butyl-2-(trifluoromethyl)-2H-benzopyran-3-carboxylic acid The synthesis method in this Example differs from that in Example 2 only in that the Grignard reagent used in step (2) is propyl magnesium bromide, which is used in a molar ratio of 4:1 to 5-sulfur pentafluoride-2-hydroxybenzaldehyde. In addition, the preparation methods and conditions are the same as those in Example 2, and by characterization via 1H NMR spectroscopy and mass spectrometry, the product is determined to have the following structure:

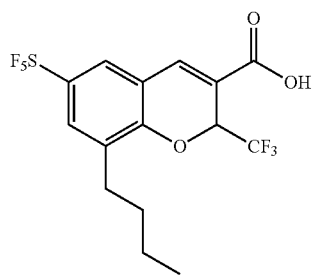

$^1$H NMR (400 MHz, CDCl$_3$) δ 7.83 (s, 1H), 7.58 (d, J=2.2 Hz, 1H), 7.51 (d, J=2.2 Hz, 1H), 5.80 (q, J=6.7 Hz, 1H), 2.80-2.55 (m, 2H), 1.59 (dt, J=15.6, 7.7 Hz, 2H), 1.38 (dq, J=14.7, 7.3 Hz, 2H), 0.95 (t, J=7.3 Hz, 3H). MS (MM−ES+APCI), m/z: 425.0 (M-H$^+$).

Example 5 Synthesis of 6-sulfur pentafluoride-8-pentyl-2-trifluoromethyl-2H-benzopyran-3-carboxylic acid The synthesis method in this Example differs from that in Example 2 only in that the Grignard reagent used in step (2) is butyl magnesium bromide, which is used in a molar ratio of 3:1 to 5-sulfur pentafluoride-2-hydroxybenzaldehyde. In addition, the preparation methods and conditions are the same as those in Example 2, and by characterization via 1H NMR spectroscopy and mass spectrometry, 6-sulfur pentafluoride-8-pentyl-2-trifluoromethyl-2H-benzopyran-3-carboxylic acid is determined to have the following structure:

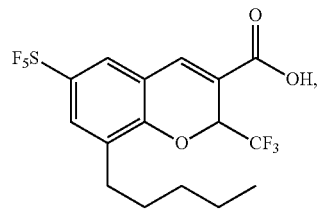

The characterization results of 1H NMR spectroscopy and mass spectrometry are as follows: $^1$H NMR (400 MHz, CDCl$_3$) δ 7.71 (s, 1H), 7.58 (d, J=2.4 Hz, 1H), 7.55-7.49 (m, 1H), 5.62 (t, J=6.9 Hz, 1H), 3.95-3.82 (m, 2H), 2.78-2.65 (m, 2H), 1.61 (dd, J=14.9, 7.5 Hz, 2H), 1.41-1.29 (m, 2H), 1.15 (t, J=7.1 Hz, 3H). MS (MM−ES+APCI), m/z: 439.0 (M-H$^+$).

Example 6 Synthesis of 6-sulfur pentafluoride-8-benzyl-2-trifluoromethyl-2H-benzopyran-3-carboxylic acid The synthesis method in this Example differs from that in Example 2 only in that the Grignard reagent used in step (2) is phenyl magnesium bromide, which is used in a molar ratio of 2:1 to 5-sulfur pentafluoride-2-hydroxybenzaldehyde. In addition, the preparation methods and conditions are the same as those in Example 2, and by characterization via 1H NMR spectroscopy and mass spectrometry, 6-sulfur pentafluoride-8-benzyl-2-trifluoromethyl-2H-benzopyran-3-carboxylic acid is determined to have the following structure:

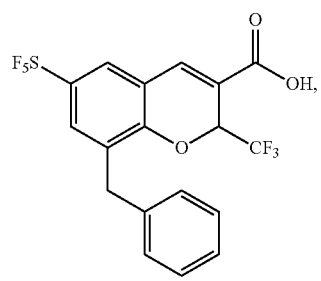

The characterization results of 1H NMR spectroscopy and mass spectrometry are as follows: $^1$H NMR (400 MHz, CDCl$_3$) δ 7.83 (s, 1H), 7.56 (s, 2H), 7.31 (t, J=7.3 Hz, 2H), 7.23 (d, J=7.4 Hz, 1H), 7.18 (d, J=7.1 Hz, 2H), 5.79 (q, J=6.6 Hz, 1H), 4.03 (d, J=3.7 Hz, 2H). MS (MM−ES+APCI), m/z: 459.0 (M-H+).

Example 7 Synthesis of 6-sulfur pentafluoride-8-(3-methyl-2-pyridylmethylene)-2-trifluoromethyl-2H-benzopyran-3-carboxylic acid The synthesis method in this Example differs from that in Example 2 only in that the Grignard reagent used in step (2) is 3-methyl-2-pyridyl magnesium bromide, which is used in a molar ratio of 2:1 to 5-sulfur pentafluoride-2-hydroxybenzaldehyde. In addition, the preparation methods and conditions are the same as those in Example 2, and by characterization via mass spectrometry, 6-sulfur pentafluoride-8- benzyl-2-trifluoromethyl-2H-benzopyran-3-carboxylic acid is determined to have the following structure:

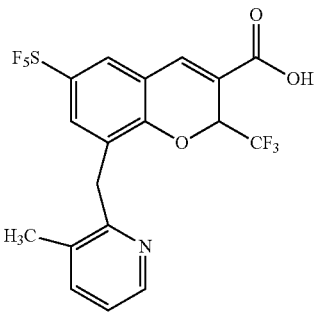

m/z: 475.0 (M-H+).

Example 8 Synthesis of (S)-6-sulfur pentafluoride-8-chloro-2-trifluoromethyl-2H-benzopyran-3-carboxylic acid The synthetic route is as follows:

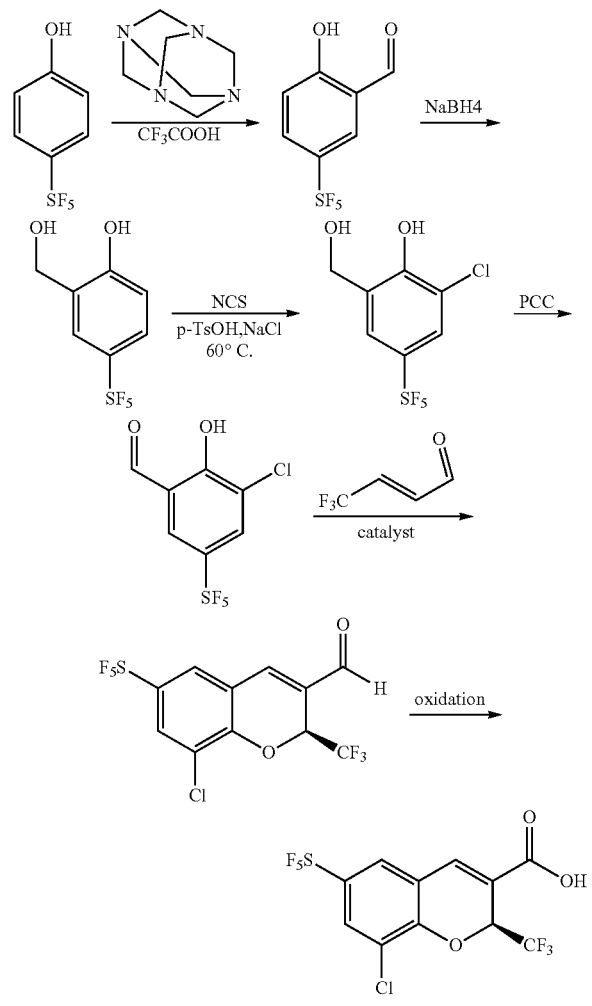

(1) Synthesis of 5-sulfur pentafluoride-2-hydroxybenzaldehyde

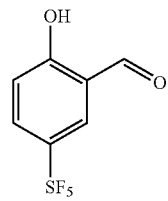

Under protection of argon, the p-sulfur pentafluoride phenol (1.0 g, 4.5 mmol) was dissolved in trifluoroacetic acid (6 mL), and then hexamethylenetetramine (1.0 g, 7.1 mmol) was slowly added to the above solution, the reaction was maintained at a temperature of 80° C. for 12 h, the reaction solution was cooled to room temperature, to which 6 mL of hydrochloric acid (3 mol/L) was added and then stirred for another 0.5 h. After the reaction was completed, the reaction solution was extracted with ethyl acetate, and the resulting organic phase was washed with brine, dried, and rotary evaporated under reduced pressure, then purified through column chromatography to give the product (0.53 g, 47%).

$^1$H NMR (400 MHz, CDCl$_3$) δ 11.31 (s, 1H), 9.94 (s, 1H), 7.99 (d, J=2.7 Hz, 1H), 7.90 (dd, J=9.2, 2.7 Hz, 1H), 7.02 (dd, J=35.3, 11.0 Hz, 1H). MS (MM−ES+APCI), m/z: 247.0 (M-H$^+$).

(2) Synthesis of 4-sulfur pentafluoride-2-hydroxymethyl-phenol

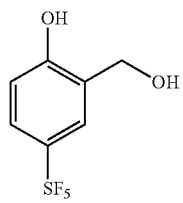

5-sulfur pentafluoride-2-hydroxybenzaldehyde (0.40 g, 1.61 mmol) and ethanol (6 mL) were added to a single-necked flask, to which solid sodium borohydride (0.080 g, 2.2 mmol) was slowly added, the mixture was heated to reflux for 2 h, then cooled to room temperature and adjusted to a pH of less than 3 with hydrochloric acid (3 mol/L), which was then extracted three times with dichloromethane (20 mL), the resulting organic phase was washed with brine, dried over anhydrous sodium sulfate for 15 minutes, rotary evaporated under reduced pressure, then purified through column chromatography to give the product (0.38 g, 94%).

$^1$H NMR (400 MHz, CDCl$_3$) δ 7.92 (s, 1H), 7.61 (d, J=9.0, 2.6 Hz, 1H), 6.92 (d, J=8.9 Hz, 1H), 4.94 (s, 2H). MS (MM−ES+APCI), m/z: 249.0 (M-H$^+$).

(3) Synthesis of 4-sulfur pentafluoride-2-hydroxymethyl-6-chlorophenol

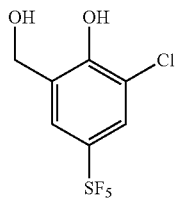

Under protection of argon, 4-sulfur pentafluoride-2-hydroxymethyl-phenol (0.38 g, 1.51 mmol), chlorosuccinimide (i.e., NCS, 0.40 g, 3.03 mmol), p-toluenesulfonic acid monohydrate (i.e., TsOH·H$_2$O, 0.58 g, 3.03 mmol), sodium chloride (0.26 g, 4.53 mmol) and saturated sodium chloride aqueous solution (2 mL) were mixed in the sealed tube, which was then sealed. The reaction system was stirred and heated at 60° C. overnight. After the reaction was completed, the reaction system was diluted with water (10 mL), and then extracted three times with ethyl acetate (10 mL), the organic phases were combined and washed with brine, dried over anhydrous sodium sulfate, and the solvent was distilled off under reduced pressure, the crude product was isolated by column chromatography to give the product (0.15 g, 35.2%).

$^1$H NMR (400 MHz, CDCl$_3$) δ 7.70 (dd, J=14.3, 3.0 Hz, 1H), 7.54 (dd, J=8.3, 2.6 Hz, 1H), 4.86 (s, 2H). MS (MM–ES+APCI), m/z: 283.0 (M-H$^+$).

(4) Synthesis of 5-sulfur pentafluoride-2-hydroxy-3-chlorobenzaldehyde

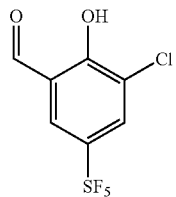

4-sulfur pentafluoride-2-hydroxymethyl-6-chlorophenol (0.15 g, 0.53 mmol), pyridinium chlorochromate (i.e., PCC, 0.23 g, 1.06 mmol) and dichloromethane (10 mL) were mixed and then stirred at room temperature overnight. After the reaction was completed, the solvent was distilled off under reduced pressure, the crude product was isolated by column chromatography to give the product (0.12 g, 80%).

$^1$H NMR (400 MHz, CDCl$_3$) δ 11.81 (s, 1H), 9.94 (s, 1H), 7.72 (dd, J=8.5, 4.1 Hz, 1H), 7.57-7.50 (dd, J=8.2, 2.7 Hz, 1H). MS (MM–ES+APCI), m/z: 281.0 (M-H$^+$).

(5) Synthesis of (S)-6-sulfur pentafluoride-8-chloro-2-trifluoromethyl-2H-benzopyran-3-formaldehyde

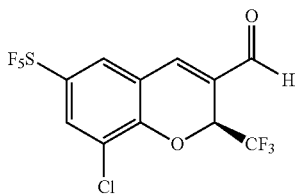

The compound 5-sulfur pentafluoride-2-hydroxy-3-chlorobenzaldehyde (0.12 g, 0.42 mmol), 4,4,4-trifluorobut-2-enal (0.10 g, 0.82 mmol), (2S)-2-[diphenyl[(trimethylsilyl)oxy]methyl]-pyrrolidine (0.026 g, 0.08 mmol), and p-nitrobenzoic acid (0.014 g, 0.08 mmol) were mixed in 50 mL ethyl acetate, then stirred overnight. After the reaction was completed, the crude product was isolated by column chromatography to give the product (0.046 g, yield 28%).

$^1$H NMR (400 MHz, CDCl$_3$) δ 9.72 (s, 1H), 8.02 (s, 1H), 7.94 (s, 1H), 7.64 (s, 1H), 5.89 (q, J=6.6 Hz, 1H). MS (MM–ES+APCI), m/z: 387.0 (M-H$^+$).

(6) Synthesis of (S)-6-sulfur pentafluoride-8-chloro-2-trifluoromethyl-2H-benzopyran-3-carboxylic acid

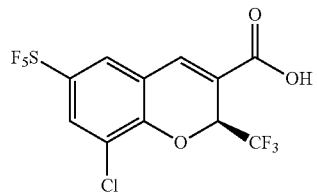

The compound (S)-6-sulfur pentafluoride-8-chloro-2-trifluoromethyl-2H-benzopyran-3-formaldehyde (0.046 g, 0.12 mmol), and potassium peroxymonosulfate complex salt (0.11 g, 0.18 mmol) were mixed in DMF (5 mL), and the mixture was stirred overnight. After the reaction was completed, water was added to the reaction system and the reaction system was extracted with ethyl acetate, the resulting organic phase was washed with saturated sodium chloride aqueous solution, dried, and rotary evaporated under reduced pressure, then purified through column chromatography to give the product (0.036 g, 75%). After analysis via chiral AD column, its EE value was higher than 92%.

$^1$H NMR (400 MHz, CDCl$_3$) δ 8.10 (s, 1H), 7.98 (s, 1H), 7.71 (s, 1H), 5.88 (q, J=6.7 Hz, 1H). MS (MM–ES+APCI), m/z: 403.0 (M-H$^+$).

Example 9 Synthesis of (S)-6-sulfur pentafluoride-8-methyl-2-trifluoromethyl-2H-benzopyran-3-carboxylic acid The synthesis method in this Example differs from that in Example 1 only in that the chiral catalyst used in the reaction of step (5) is 2-[diphenyl[(trimethylsilyl)oxy]methyl]-pyrrolidine, which is used in a molar ratio of 4:1 to 5-sulfur pentafluoride-2-hydroxy-3-methylbenzaldehyde. In addition, the preparation methods and conditions are the same as those in Example 1, and by characterization via 1H NMR spectroscopy and mass spectrometry, (S)-6-sulfur pentafluoride-8-methyl-2-trifluoromethyl-2H-benzopyran-3-carboxylic acid is determined to have the following structure:

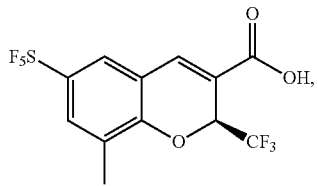

¹H NMR (400 MHz, CDCl₃) δ 7.63 (s, 1H), 7.56 (s, 1H), 7.54 (s, 1H), 5.81 (q, J=6.7 Hz, 1H), 2.32 (s, 3H). After analysis via chiral AD column, its EE value was higher than 92%.

Applicant has stated that although the detailed methods of the present disclosure have been described by the above Examples, the present disclosure is not limited thereto, that is to say, it is not meant that the present disclosure has to be implemented depending on the above detailed methods. It will be apparent to those skilled in the art that any improvements made to the present disclosure, equivalent replacements and addition of adjuvant ingredients to the raw materials of the products of the present disclosure, and selections of the specific implementations, etc., all fall within the protection scope and the disclosed scope of the present disclosure.

The invention claimed is:

1. A 4-sulfur pentafluoride phenol-based compound, wherein the compound has a structure as shown by formula II below:

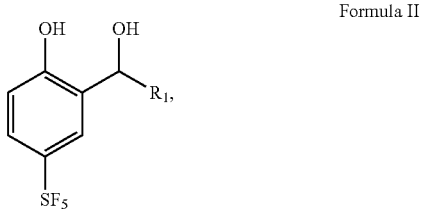

Formula II wherein $R_1$ is any one selected from a group consisting of hydrogen, ethyl, propyl, isopropyl, butyl, isobutyl, tert-butyl, pentyl, isopentyl, neopentyl, $C_6$-$C_{15}$ alkylaryl and $C_3$-$C_8$ heterocyclic radical.

2. The 4-sulfur pentafluoride phenol-based compound according to claim 1, wherein $R_1$ is any one selected from a group consisting of $C_6$-$C_{11}$ alkylaryl and $C_4$-$C_6$ heterocyclic radical.

3. The 4-sulfur pentafluoride phenol-based compound according to claim 2, wherein $R_1$ is any one selected from a group consisting of phenyl, benzyl, substituted benzyl and

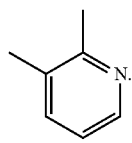

4. A preparation method for the 4-sulfur pentafluoride phenol-based compound of claim 1, wherein the preparation method comprises the following steps: compound I reacts with sodium borohydride or a Grignard reagent to obtain compound II, as shown by the following reaction formula:

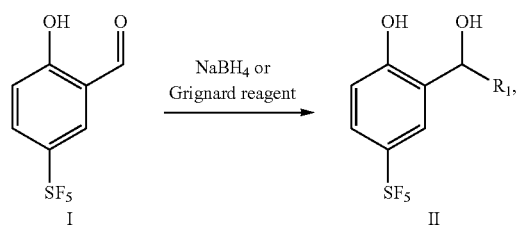

wherein, $R_1$ is any one selected from a group consisting of hydrogen, $C_1$-$C_{10}$ alkyl, $C_6$-$C_{15}$ alkylaryl and $C_3$-$C_8$ heterocyclic radical, wherein compound I is prepared by using 4-sulfur pentafluoride phenol as a raw material, and the preparation method is as follows: 4-sulfur pentafluoride phenol reacts with hexamethylenetetramine in an acid solution to obtain compound I, as shown by the following reaction formula:

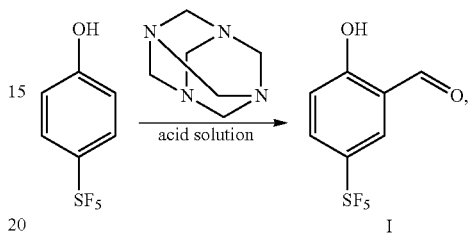

wherein the acid solution is any one or a combination of at least two selected from a group consisting of polyphosphoric acid, glacial acetic acid and trifluoroacetic acid, wherein the molar ratio of 4-sulfur pentafluoride phenol to hexamethylenetetramine is from 1:1.2 to 1:2, wherein the acid solution is used in an amount from 5 to 15 mL on the basis of 1 g of 4-sulfur pentafluoride phenol, wherein the temperature at which 4-sulfur pentafluoride phenol and hexamethylenetetramine react in an acid solution is from 70° C. to 90° C., and wherein the time for the reaction between 4-sulfur pentafluoride phenol and hexamethylenetetramine in an acid solution is from 5 to 24 hours.

5. A preparation method for 4-sulfur pentafluoride phenol-based compound according to claim 1, wherein the preparation method comprises the following steps: compound I reacts with sodium borohydride or a Grignard reagent to obtain compound II, as shown by the following reaction formula:

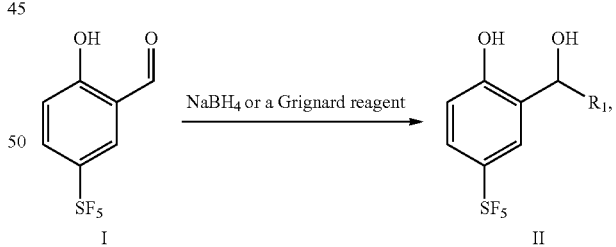

wherein, $R_1$ is any one selected from a group consisting of hydrogen, $C_1$-$C_{10}$ alkyl, $C_6$-$C_{15}$ alkylaryl and $C_3$-$C_8$ heterocyclic radical, wherein the Grignard reagent has a molecular formula of $R_3MgX$, $R_3$ is any one selected from a group consisting of $C_1$-$C_{10}$ alkyl, $C_6$-$C_{15}$ alkylaryl and $C_3$-$C_8$ heterocyclic radical, and X is a halogen;

wherein the molar ratio of compound I to sodium borohydride or the Grignard reagent is from 1:2 to 1:4;

wherein the solvent for the reaction between compound I and sodium borohydride or a Grignard reagent is $C_1$-$C_4$ alcohol;

wherein the solvent is used in an amount from 10 to 20 mL on the basis of 1 g of compound I;

wherein the reaction of compound I with sodium borohydride or a Grignard reagent is carried out under a reflux condition;

wherein the time for the reaction between compound I and sodium borohydride or a Grignard reagent is from 1 to 5 hours.

6. A 4-sulfur pentafluoride phenol-based compound, wherein the compound has a structure as shown by the formula III(b) below:

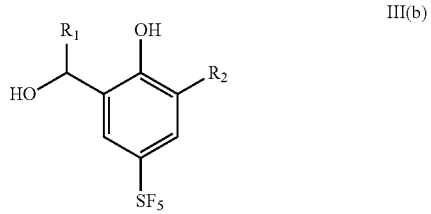

wherein, $R_1$ is any one selected from a group consisting of hydrogen, $C_1$-$C_{10}$ alkyl, $C_6$-$C_{15}$ alkylaryl and $C_3$-$C_8$ heterocyclic radical, and $R_2$ is halogen.

7. The 4-sulfur pentafluoride phenol-based compound according to claim 6, wherein $R_1$ is any one selected from a group consisting of $C_1$-$C_8$ alkyl, $C_6$-$C_{11}$ alkylaryl and $C_4$-$C_6$ heterocyclic radical.

8. The 4-sulfur pentafluoride phenol-based compound according to claim 7, wherein $R_1$ is any one selected from a group consisting of methyl, ethyl, propyl, isopropyl, butyl, isobutyl, tert-butyl, pentyl, isopentyl, neopentyl, phenyl, benzyl, substituted benzyl and

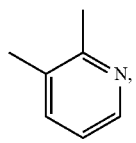

and $R_2$ is selected from a group consisting of F, Br, Cl and I.

9. A preparation method for 4-sulfur pentafluoride phenol-based compound according to claim 6, wherein the method comprises the following steps: compound II reacts with a halogenation reagent to obtain compound III (b), as shown by the following reaction formula:

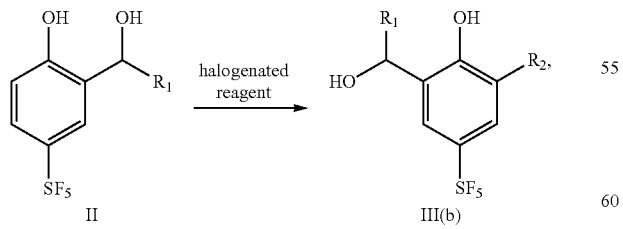

wherein, $R_1$ is any one selected from a group consisting of hydrogen, $C_1$-$C_{10}$ alkyl, $C_6$-$C_{15}$ alkylaryl and $C_3$-$C_8$ heterocyclic radical, and $R_2$ is halogen, wherein the halogenation reagent is N-chlorosuccinimide and/or N-bromosuccinimide;

wherein the molar ratio of compound II to a halogenation reagent is from 1:2 to 1:4;

wherein the reaction temperature is from 60° C. to 100° C.;

wherein the reaction time is from 8 to 24 hours.

10. A preparation method for a sulfur pentafluoride substituted benzopyran-based compound, wherein the method comprises the following steps:

(1) Compound II reacts with chloroformate, and then reacts with sodium borohydride to obtain compound III (a), as shown by the following reaction formula:

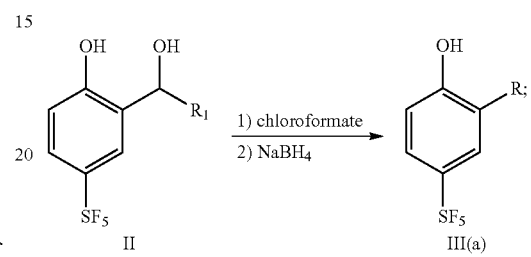

(2) Compound III (a) reacts with hexamethylenetetramine in an acid solution to obtain compound IV, as shown by the following reaction formula:

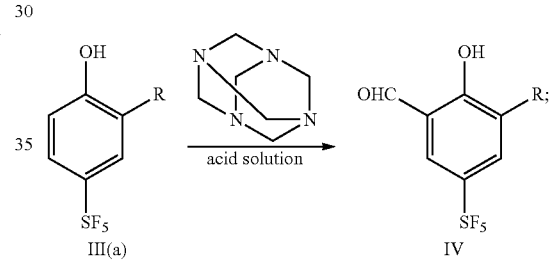

(3) Compound IV reacts with ethyl 4,4,4-trifluorocrotonate and a weak base in a solvent to obtain compound V, as shown by the following reaction formula:

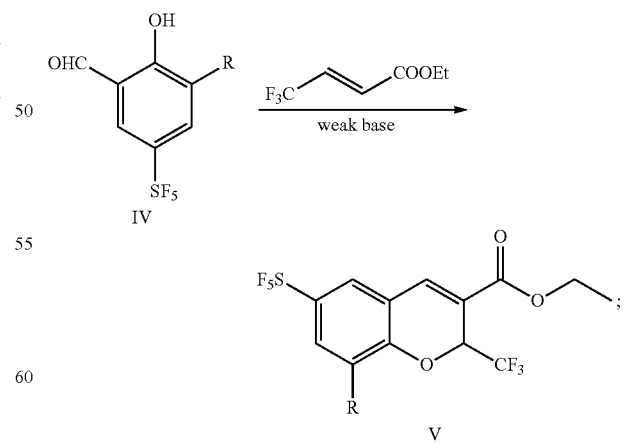

(4) Compound V is hydrolyzed with a base, and then neutralized with an acid to obtain product VI, as shown by the following reaction formula:

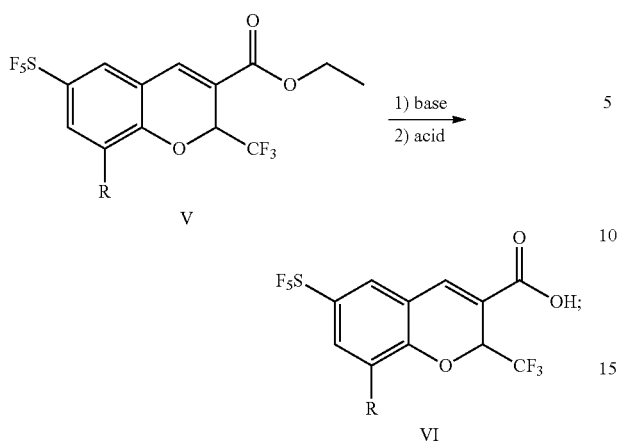

wherein, each of $R_1$ and R is any one independently selected from a group consisting of hydrogen, $C_1$-$C_{10}$ alkyl, $C_6$-$C_{15}$ alkylaryl and $C_3$-$C_8$ heterocyclic radical.

11. The preparation method according to claim 10,
wherein the chloroformate in step (1) is any one or a combination of at least two selected from a group consisting of methyl chloroformate, ethyl chloroformate, propyl chloroformate and butyl chloroformate,
wherein the molar ratio of compound II to chloroformate in step (1) is from 1:2 to 1:3;
wherein the molar ratio of compound II to sodium borohydride in step (1) is from 1:8 to 1:10;
wherein the solvent used in the reaction of compound II with chloroformate in step (1) is dichloromethane and/or chloroform;
wherein the reaction of compound II with chloroformate in step (1) is carried out in the presence of a weakly basic substance;
wherein the molar ratio of compound II to the weakly basic substance is from 1:2 to 1:10;
wherein the temperature for the reaction between compound II and chloroformate in step (1) is from 0° C. to 30° C.;
wherein the time for the reaction between compound II and chloroformate in step (1) is from 1 to 5 hours;
wherein the temperature for the reaction between compound II and sodium borohydride in step (1) is from 0° C. to 30° C.;
wherein the time for the reaction between compound II and sodium borohydride in step (1) is from 1 to 5 hours;
wherein the acid solution in step (2) is any one or a combination of at least two selected from a group consisting of trifluoroacetic acid, polyphosphoric acid and glacial acetic acid;
wherein the molar ratio of compound III(a) to hexamethylenetetramine in step (2) is from 1:1.2 to 1:2;
wherein the amount of the acid solution used in step (2) is from 10 to 30 mL on the basis of 1 g of compound III(a);
wherein the reaction temperature in step (2) is from 60° C. to 100° C.;
wherein the reaction time in step (2) is from 8 to 48 hours;
wherein the molar ratio of compound IV to ethyl 4,4,4-trifluorocrotonate in step (3) is from 1:1.2 to 1:10;
wherein the weak base in step (3) is any one or a combination of at least two selected from a group consisting of triethylamine, potassium carbonate, cesium carbonate and cesium fluoride;
wherein the amount of the weak base used in step (3) is from 10 to 20 mL on the basis of 1 g of compound IV;
wherein the solvent used in step (3) is any one or a combination of at least two selected from a group consisting of triethylamine, tetrahydrofuran, N,N-dimethylformamide and dimethyl sulfoxide;
wherein the reaction temperature in step (3) is from 80° C. to 120° C.;
wherein the reaction time in step (3) is from 10 to 72 hours;
wherein the base in step (4) is any one or a combination of at least two selected from a group consisting of potassium hydroxide, sodium hydroxide and lithium hydroxide;
wherein the molar ratio of compound V to the base in step (4) is from 1:10 to 1:20;
wherein the temperature for the hydrolysis with a base in step (4) is from 20° C. to 30° C.;
wherein the time for the hydrolysis with a base in step (4) is from 1 to 5 hours;
wherein the acid in step (4) is hydrochloric acid and/or sulfuric acid.

12. The preparation method according to claim 11, wherein the preparation method comprises the following steps:

(1) 4-sulfur pentafluoride phenol reacts with hexamethylenetetramine in trifluoroacetic acid to obtain compound I, as shown by the following reaction formula:

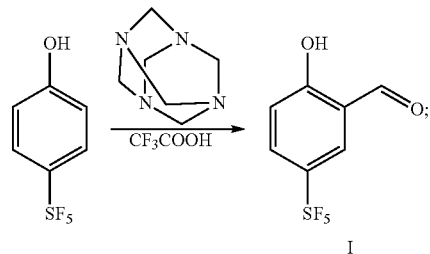

(2) Compound I reacts with sodium borohydride or a Grignard reagent to obtain compound II, as shown by the following reaction formula:

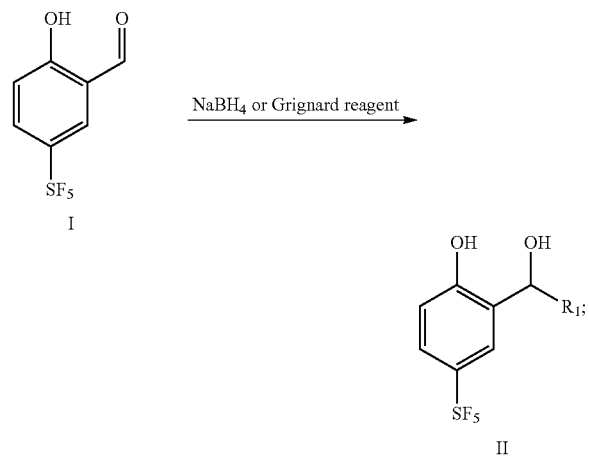

(3) Compound II reacts with ethyl chloroformate in the presence of triethylamine, and then reacts with sodium borohydride to obtain compound III (a), as shown by the following reaction formula:

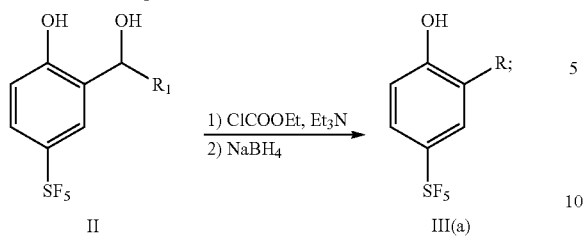

(4) Compound III (a) reacts with hexamethylenetetramine in trifluoroacetic acid to obtain compound IV, as shown by the following reaction formula:

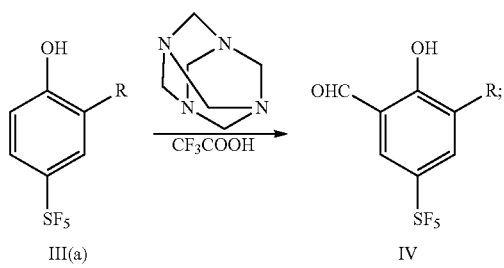

(5) Compound IV reacts with ethyl 4,4,4-trifluorocrotonate and triethylamine in a solvent to obtain compound V, as shown by the following reaction formula:

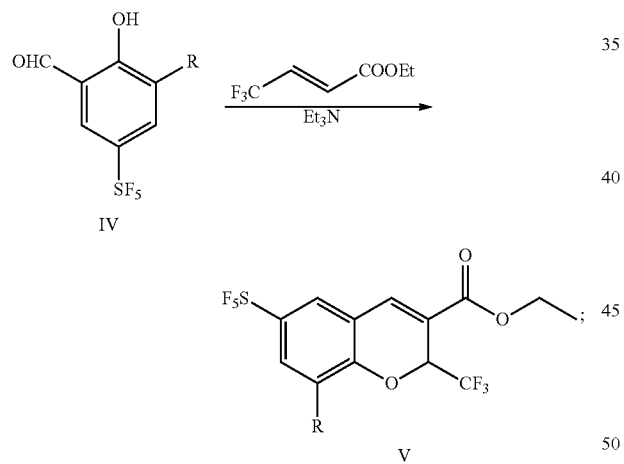

(6) Compound V is hydrolyzed with a base, and then neutralized with an acid to obtain product VI, as shown by the following reaction formula:

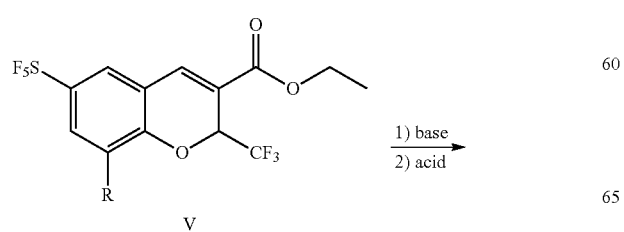

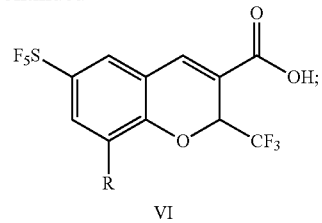

wherein, each of R1 and R is any one independently selected from a group consisting of hydrogen, $C_1$-$C_{10}$ alkyl, $C_6$-$C_{15}$ alkylaryl and $C_3$-$C_8$ heterocyclic radical.

13. The preparation method according to claim 12, wherein product VI is a racemate compound, and in order to obtain a chiral compound thereof, a chiral catalyst is added to the reaction of compound IV with ethyl 4,4,4-trifluorocrotonate.

14. The preparation method according to claim 13, wherein the chiral catalyst is a diphenylprolinol silyl ether-based compound or a dinaphthylprolinol silyl ether-based compound, and
wherein the molar ratio of the chiral catalyst to compound IV is from 1:4 to 1:6.

15. A preparation method for a sulfur pentafluoride substituted benzopyran-based compound, wherein the preparation method comprises the following steps:

A. compound III (b) reacts with an oxidant to obtain compound IV (b), as shown by the following reaction formula:

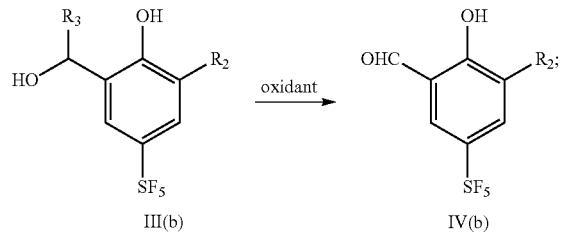

B. Compound IV (b) reacts with ethyl 4,4,4-trifluorocrotonate and a weak base in a solvent to obtain compound V(b), as shown by the following reaction formula:

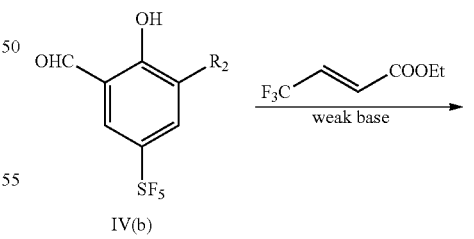

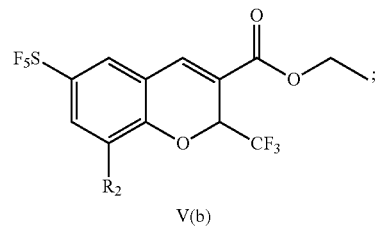

C. Compound V (b) is hydrolyzed with a base, and then neutralized with an acid to obtain the product VI (b), as shown by the following reaction formula:

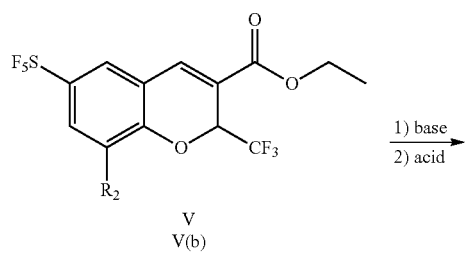

wherein, $R_1$ is any one selected from a group consisting of hydrogen, $C_1$-$C_{10}$ alkyl, $C_6$-$C_{15}$ alkylaryl and $C_3$-$C_8$ heterocyclic radical, and $R_2$ is halogen.

16. The preparation method according to claim 15, wherein:
the oxidant in step A is pyridinium chlorochromate and/or manganese dioxide;
the molar ratio of compound III (b) to the oxidant in step A is from 1:2 to 1:20;
the reaction temperature in step A is from 10° C. to 30° C.;
the reaction time in step A is from 5 to 24 hours;
the molar ratio of compound IV (b) to ethyl 4,4,4-trifluorocrotonate in step B is from 1:1.2 to 1:10;
the weak base in step B is any one or a combination of at least two selected from a group consisting of triethylamine, potassium carbonate, cesium carbonate and cesium fluoride;
the amount of the weak base used in step B is from 10 to 20 mL on the basis of 1 g of compound IV(b);
the solvent in step B is any one or a combination of at least two selected from a group consisting of triethylamine, tetrahydrofuran, N,N-dimethylformamide and dimethyl sulfoxide;
the reaction temperature in step B is from 80° C. to 120° C.;
the reaction time in step B is from 10 to 72 hours;
the base in step C is any one or a combination of at least two selected from a group consisting of potassium hydroxide, sodium hydroxide and lithium hydroxide;
the molar ratio of compound V(b) to the base in step C is from 1:10 to 1:20;
the temperature for the hydrolysis with a base in step C is from 20° C. to 30° C.;
the time for the hydrolysis with a base in step C is from 1 to 5 hours;
the acid in step C is hydrochloric acid and/or sulfuric acid.

17. A preparation method for compound VI(b), wherein the method comprises the following steps:
(1) 4-sulfur pentafluoride phenol reacts with hexamethylenetetramine in an acid solution to obtain compound I, as shown by the following reaction formula:

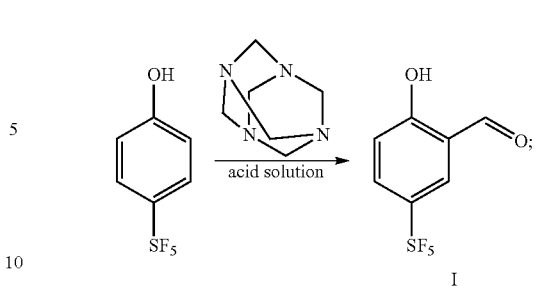

(2) compound I reacts with sodium borohydride or a Grignard reagent to obtain compound II, as shown by the following reaction formula:

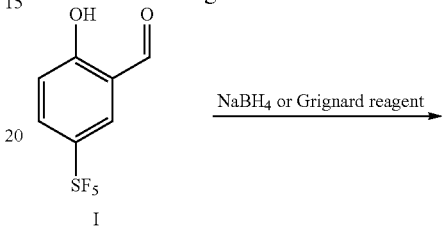

(3) Compound II reacts with a reagent to obtain compound III (b), as shown by the following reaction formula:

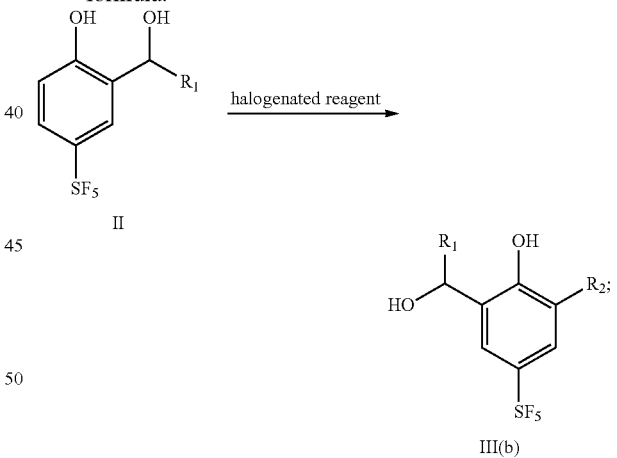

(4) compound III(b) reacts with an oxidant to obtain compound IV(b), as shown by the following reaction formula:

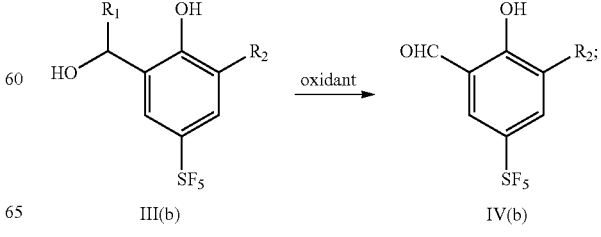

(5) Compound IV(b) reacts with ethyl 4,4,4-trifluorocrotonate and a weak base in a solvent to obtain compound V, as shown by the following reaction formula:

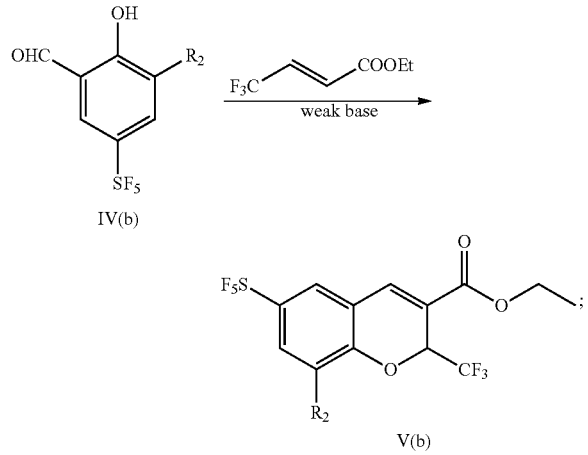

(6) Compound V(b) is hydrolyzed with a base, and then neutralized with an acid to obtain product VI(b), as shown by the following reaction formula:

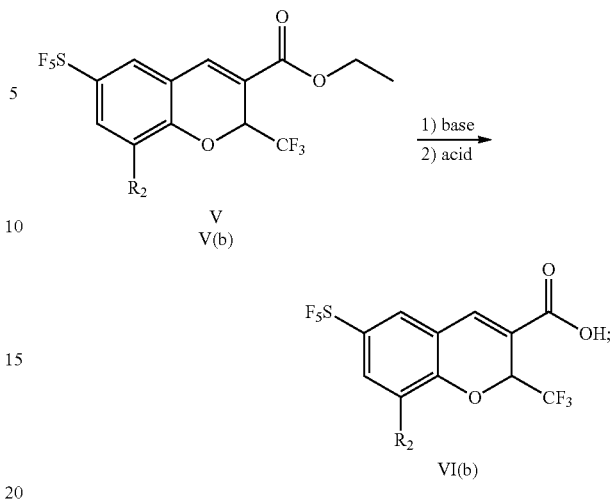

wherein, $R_1$ is any one selected from a group consisting of hydrogen, $C_1$-$C_{10}$ alkyl, $C_6$-$C_{15}$ alkylaryl and $C_3$-$C_8$ heterocyclic radical, and $R_2$ is halogen.

* * * * *